United States Patent
Kawachi et al.

(10) Patent No.: US 9,135,557 B2
(45) Date of Patent: Sep. 15, 2015

(54) INTERNAL ABNORMALITY DIAGNOSIS METHOD, INTERNAL ABNORMALITY DIAGNOSIS SYSTEM, AND DECISION TREE GENERATION METHOD FOR INTERNAL ABNORMALITY DIAGNOSIS OF OIL-FILLED ELECTRIC APPARATUS UTILIZING GAS CONCENTRATION IN OIL

(75) Inventors: Fumio Kawachi, Osaka (JP); Masanori Yamakoshi, Osaka (JP); Makoto Kasaoka, Osaka (JP)

(73) Assignee: KANDEN ENGINEERING CORPORATION, Osaka-shi (JP)

( * ) Notice: Subject to any disclaimer, the term of this patent is extended or adjusted under 35 U.S.C. 154(b) by 340 days.

(21) Appl. No.: 13/820,663

(22) PCT Filed: Sep. 2, 2010

(86) PCT No.: PCT/JP2010/065022
§ 371 (c)(1),
(2), (4) Date: Apr. 19, 2013

(87) PCT Pub. No.: WO2012/029154
PCT Pub. Date: Mar. 8, 2012

(65) Prior Publication Data
US 2013/0204827 A1    Aug. 8, 2013

(51) Int. Cl.
*G06F 17/00* (2006.01)
*H01F 27/40* (2006.01)
(Continued)

(52) U.S. Cl.
CPC .............. *G06N 5/02* (2013.01); *G01N 33/2841* (2013.01)

(58) Field of Classification Search
None
See application file for complete search history.

(56) References Cited

U.S. PATENT DOCUMENTS 4,502,320 A    3/1985   Sakai et al.

FOREIGN PATENT DOCUMENTS

| JP | 58-18909 A | 2/1983 |
| JP | 6-4292 A | 1/1994 |
| JP | 6-113439 A | 4/1994 |

(Continued)

OTHER PUBLICATIONS

Wang, Xi-Zhao, Ming-Zhu Lu, and Jian-Bing Huo. "Fault diagnosis of power transformer based on large margin learning classifier." Machine Learning and Cybernetics, 2006 International Conference on. IEEE, 2006.*

(Continued)

*Primary Examiner* — Jeffrey A Gaffin
*Assistant Examiner* — David H Kim
(74) *Attorney, Agent, or Firm* — Westerman, Hattori, Daniels & Adrian, LLP

(57) ABSTRACT

The present invention provides a method for generating a decision tree for determining the type of an internal abnormality of an oil-filled electric apparatus using a computer. In the decision tree generation method, the computer generates a standardized data group by converting concentrations of a plurality of gas species dissolved in an insulating oil in an oil-filled electric apparatus into ratios for each abnormality case, generates a discretized data group by converting the ratios of the concentrations of the gas species, the ratios constituting the standardized data group, into a plurality of discretized attributes using predetermined thresholds which are set for the respective gas species, and generates a decision tree for determining the type of an internal abnormality of the oil-filled electric apparatus by analysis using specific formulae on the basis of the discretized data group.

8 Claims, 16 Drawing Sheets

(51) Int. Cl.
*G06N 5/02* (2006.01)
*G01N 33/28* (2006.01)

(56) References Cited

FOREIGN PATENT DOCUMENTS

| JP | 8-161172 A | 6/1996 |
|---|---|---|
| JP | 2001-69659 A | 3/2001 |
| JP | 2002-350426 A | 12/2002 |
| JP | 2005-107940 A | 4/2005 |
| JP | 2005-252167 A | 9/2005 |
| JP | 2007-213441 A | 8/2007 |

OTHER PUBLICATIONS

Feng Zhao; Hongsheng Su, "A decision tree approach for power transformer insulation fault diagnosis," Intelligent Control and Automation, 2008. WCICA 2008. 7th World Congress on , vol., No., pp. 6882,6886, Jun. 25-27, 2008.*
Electric Technology Research Association, Ogawa, "Electric Joint Research, Repair Guideline for Power Transformer", vol. 65, No. 1, Sep. 5, 2009, pp. 48-51 (cited in specification).
Umano et al., "Generation of fuzzy decision trees by extended ID3 algorithm and its applicaiton to diagnosis by analyzing gas in oil" Proceeding of the fourth Intelligent FA Symposium, ISCIE, Jul. 7-8, 1993, pp. 201-204 (cited in specification and ISR).
Mang-Hui Wang, "A Novel Extension Method for Transformer Fault Diagnosis", IEEE Transactions on Power Delivery, vol. 18, No. 1, Jan. 1993, pp. 164-169 (cited in ISR).
C.E. Lin et al., "An Expert System for Transformer Fault Diagnosis Using Dissolved Gas Analysis", IEEE Transactions on Power Delivery, vol. 18, No. 1, Jan. 1993, pp. 232-238 (cited in ISR).
International Search Report for PCT/JP2010/065022, mailing date of Oct. 5, 2010.

* cited by examiner

Fig. 8

| Gas species (x) | Gas concentration (ppm) | | |
|---|---|---|---|
| | Case 1 | Case 2 | ....... |
| Gas 1 | $a_{11}$ | $a_{21}$ | |
| Gas 2 | $a_{12}$ | $a_{22}$ | |
| Gas 3 | $a_{13}$ | $a_{23}$ | ....... |
| Gas 4 | $a_{14}$ | $a_{24}$ | |
| Gas 5 | $a_{15}$ | $a_{25}$ | |
| ⋮ | ⋮ | ⋮ | |
| Total | $\Sigma a_{1p}$ | $\Sigma a_{2p}$ | ....... |
| Abnormality type | Abnormality 1 | Abnormality 2 | ....... |

Fig. 9

| Gas species (x) | Standardized Gas ratio (-) | | |
|---|---|---|---|
| | Case 1 | Case 2 | ....... |
| Gas 1 | $a_{11}/\Sigma a_{1p}$ | $a_{21}/\Sigma a_{2p}$ | |
| Gas 2 | $a_{12}/\Sigma a_{1p}$ | $a_{22}/\Sigma a_{2p}$ | |
| Gas 3 | $a_{13}/\Sigma a_{1p}$ | $a_{23}/\Sigma a_{2p}$ | |
| Gas 4 | $a_{14}/\Sigma a_{1p}$ | $a_{24}/\Sigma a_{2p}$ | ....... |
| Gas 5 | $a_{15}/\Sigma a_{1p}$ | $a_{25}/\Sigma a_{2p}$ | |
| ⋮ | ⋮ | ⋮ | |
| Internal abnormality type | Abnormality 1 | Abnormality 2 | ....... |

Fig. 10

| Gas species (x) | Discretized | | |
|---|---|---|---|
| | Case 1 | Case 2 | ....... |
| Gas 1 | Extremely small amount | Small amount | |
| Gas 2 | Large amount | Extremely small amount | |
| Gas 3 | Extremely small amount | Extremely small amount | ....... |
| Gas 4 | Extremely small amount | Large amount | |
| Gas 5 | Extremely small amount | Large amount | |
| ⋮ | ⋮ | ⋮ | |
| Abnormality type | Abnormality 1 | Abnormality 2 | ....... |

Fig. 11

| Regarding gas x | | Criterion variable (class) | | | | | Total |
|---|---|---|---|---|---|---|---|
| | | Abnormality 1 | Abnormality 2 | Abnormality 3 | Abnormality 4 | Abnormality 5 | |
| Discretized attribute | Extremely small amount | $\beta_{11}$ | $\beta_{12}$ | $\beta_{13}$ | $\beta_{14}$ | $\beta_{15}$ | $\alpha_1$ |
| | Small amount | $\beta_{21}$ | $\beta_{22}$ | $\beta_{23}$ | $\beta_{24}$ | $\beta_{25}$ | $\alpha_2$ |
| | Large amount | $\beta_{31}$ | $\beta_{32}$ | $\beta_{33}$ | $\beta_{34}$ | $\beta_{35}$ | $\alpha_3$ |
| Total | | $C_1$ | $C_2$ | $C_3$ | $C_4$ | $C_5$ | $|D|$ |

Fig. 15

| Discretized attribute | Gas species (x) | | | | | ... | Internal abnormality type |
|---|---|---|---|---|---|---|---|
| | Gas 1 | Gas 2 | Gas 3 | Gas 4 | Gas 5 | ... | |
| Large amount | 0.00 | 0.00 | 1.00 | 0.15 | 0.00 | ... | Abnormality 1 |
| Small amount | 0.40 | 0.00 | 0.00 | 0.85 | 1.00 | ... | |
| Extremely small amount | 0.60 | 1.00 | 0.00 | 0.00 | 0.00 | ... | |

INTERNAL ABNORMALITY DIAGNOSIS METHOD, INTERNAL ABNORMALITY DIAGNOSIS SYSTEM, AND DECISION TREE GENERATION METHOD FOR INTERNAL ABNORMALITY DIAGNOSIS OF OIL-FILLED ELECTRIC APPARATUS UTILIZING GAS CONCENTRATION IN OIL

TECHNICAL FIELD

The present invention relates to an internal abnormality diagnosis method, an internal abnormality diagnosis system, and a decision tree generation method for internal abnormality diagnosis of an oil-filled electric apparatus utilizing gas concentration in oil.

BACKGROUND ART

There has been widely used a method of analysis using gas concentration in oil as a maintenance method for an oil-filled electric apparatus. For example, when an abnormality occurs inside an oil-filled electric apparatus such as a transformer which is in operation, there is used a so-called gas pattern method (Non Patent Document 1) or the like in which the gas concentration in oil of a sample oil which is taken from the oil-filled electric apparatus is measured, a detail and a location of the abnormality are estimated from the type of gas in oil and the concentration pattern thereof on the basis of past cases.

However, in such an analysis method, since a diagnostic specialist performs the estimation from the measured data on the basis of past cases by using his/her knowledge obtained from experience as a criterion for determination, a result of the diagnosis may vary due to a difference in the level of knowledge or experience between diagnostic specialists. Further, there is a limit on the number of diagnoses which each diagnostic specialist can deal with, and it takes time to deal with a huge number of diagnoses. Therefore, replacement or repair of an oil-filled electric apparatus may not be able to be performed at an appropriate time. Further, it requires a considerable amount of time to train a diagnostic specialist of a certain level, and a heavy burden is therefore imposed on skilled diagnostic specialists in the present circumstances.

In order to improve such a situation, an attempt for performing diagnosis using a machine has been made (Non Patent Document 2). In Non Patent Document 2, there is described an example in which a fuzzy decision tree based on ID3 algorithm is applied to analysis and diagnosis of gas in oil. In this example, when generating a fuzzy decision tree, measured values of the concentrations of a plurality of gas species are employed without change to form a fuzzy set and generate discretized data converted into a plurality of discretized attributes. However, when the measured values of the gas concentrations are used without change in this manner, relationships among the plurality of gas species are not considered. Therefore, this method diverges from a determination method by a diagnostic specialist, and therefore has a limit on accuracy as diagnosis using a machine.

Further, although various proposals have been made regarding a diagnosis method and a prediction method using a decision tree (see Patent Documents 1 and 2, for example), a method using a decision tree that can be applied to analysis of gas in oil has not yet been proposed, and a development of such a method has therefore been expected.

CITATION LIST

Patent Literature

Patent Document 1: JP-A No. H06-113439
Patent Document 2: JP-A No. 2005-107940

Non Patent Literature

Non Patent Document 1: Electric Technology Research Association, Ogawa, "Electric Joint Research, Repair Guideline for Power Transformer", Vol. 65, No. 1, P. 48-51, Sep. 5, 2009
Non Patent Document 2: Umano et al., "Generation of fuzzy decision trees by extended ID3 algorithm and its application to diagnosis by analyzing gas in oil" Proceeding of the fourth Intelligent FA Symposium, ISCIE, p. 201-204, Jul. 7-8, 1993

SUMMARY OF INVENTION

Technical Problem

It is therefore an object of the present invention to provide an internal abnormality diagnosis method, an internal abnormality diagnosis system, and a decision tree generation method for internal abnormality diagnosis of an oil-filled electric apparatus utilizing gas concentration in oil and having a diagnostic accuracy equal to or higher than that of a diagnostic specialist having reached a certain level.

Solution to Problem

In order to solve the above problems, the present invention constructs an abnormality diagnosis method of an oil-filled electric apparatus in which an internal abnormality of an oil-filled electric apparatus is diagnosed using a computer, the method comprising the steps, by a computer, of:
generating, on the basis of historical abnormality case data of an oil-filled electric apparatus, the historical abnormality case data being stored in performance data storage means, a standardized data group by converting concentrations of a plurality of gas species dissolved in an insulating oil in the oil-filled electric apparatus into ratios for each of abnormality cases, and storing the standardized data group in first standardized data group storage means;
generating, on the basis of the standardized data group of each of the abnormality cases, the standardized data group being stored in the first standardized data group storage means, a discretized data group by converting the ratios of the concentrations of the gas species, the ratios constituting the standardized data group, into a plurality of discretized attributes using predetermined thresholds set for the respective gas species, and storing the discretized data group in first discretized data group storage means;
generating a decision tree for determining a type of an internal abnormality of an oil-filled electric apparatus by analysis using the following formulae (1) to (4) on the basis of the discretized data group of each of the abnormality cases, the discretized data group being stored in the first discretized data group storage means, and storing the decision tree in decision tree storage means;
generating a standardized data group by converting concentrations of a plurality of gas species dissolved in an insulating oil taken from a determination target oil-filled electric apparatus into ratios, and storing the standardized data group in second standardized data group storage means;

generating, on the basis of the standardized data group of the determination target apparatus, the standardized data group being stored in the second standardized data group storage means, a discretized data group by converting the ratios of the concentrations of the gas species, the ratios constituting the standardized data group, into a plurality of discretized attributes using the same predetermined thresholds as in the abnormality cases, the predetermined thresholds being set for the respective gas species, and storing the discretized data group in second discretized data group storage means; and determining a type of an internal abnormality of the determination target apparatus by using the discretized data group of the determination target apparatus, the discretized data group being stored in the second discretized data group storage means, and the decision tree stored in the decision tree storage means.

[Mathematical 1]

$$G(X) = \frac{M(D) - E(X)}{S(X)} \quad \text{Formula (1)}$$

[Mathematical 2]

$$M(D) = \sum_{i=l}^{n} \left[ -\frac{C_i}{|D|} \log_2 \frac{C_i}{|D|} \right] \quad \text{Formula (2)}$$

[Mathematical 3]

$$E(X) = \sum_{j=l}^{v} \left[ \frac{\alpha_j}{|D|} \sum_{k=l}^{m} \left[ -\frac{\beta_{jk}}{\alpha_j} \log_2 \frac{\beta_{jk}}{\alpha_j} \right] \right] \quad \text{Formula (3)}$$

[Mathematical 4]

$$S(X) = \sum_{j=l}^{v} \left[ -\frac{\alpha_j}{|D|} \log_2 \frac{\alpha_j}{|D|} \right] \quad \text{Formula (4)}$$

X: a gas species dissolved in an insulating oil
D: a set of abnormality case data mapped to a node
|D|: the number of pieces of abnormality case data mapped to a node
$C_i$: the number of the i-th type of internal abnormalities in a set D
$\alpha_j$: the number of pieces of abnormality case data at the j-th branch of a gas species X
$\beta_{jk}$: the number of the k-th type of internal abnormalities at the j-th branch of a gas species X
G (X): a gain ratio
M (D): the amount of expected information with respect to the type of the internal abnormality in a set D
E (X): the amount of expected information after classification by a gas species X
S (X): the amount of expected information with respect to a gas species X in a set D
l: the type or a number of a discretized attribute of the first internal abnormality in a set D
m, n: the total number of types of internal abnormalities in a set D
v: the total number of discretized attributes In the present invention, the computer may determine as to whether or not the gas concentrations of the plurality of gas species dissolved in the insulating oil taken from the determination target oil-filled electric apparatus fall within respective predetermined normal ranges, and perform abnormality determination using the decision tree only when there is an abnormal gas species.

Further, the present invention constructs an abnormality diagnosis system of an oil-filled electric apparatus comprising a computer, the computer diagnosing an internal abnormality of an oil-filled electric apparatus, the computer including:

performance data storage means for storing historical abnormality case data of an oil-filled electric apparatus;

first standardized data group generation means for generating, on the basis of historical abnormality case data of the oil-filled electric apparatus, the historical abnormality case data being stored in the performance data storage means, a standardized data group by converting concentrations of a plurality of gas species dissolved in an insulating oil in the oil-filled electric apparatus into ratios for each of abnormality cases;

first standardized data group storage means for storing the standardized data group generated by the first standardized data group generation means;

first discretized data group generation means for generating, on the basis of the standardized data group of each of the abnormality cases, the standardized data group being stored in the first standardized data group storage means, a discretized data group by converting the ratios of the concentrations of the gas species, the ratios constituting the standardized data group, into a plurality of discretized attributes using predetermined thresholds set for the respective gas species;

first discretized data group storage means for storing the discretized data group generated by the first discretized data group generation means;

decision tree generation means for generating a decision tree for determining a type of an internal abnormality of an oil-filled electric apparatus by analysis using the following formulae (1) to (4) on the basis of the discretized data group of each of the abnormality cases, the discretized data group being stored in the first discretized data group storage means;

decision tree storage means for storing the decision tree generated by the decision tree generation means;

second standardized data group generation means for generating a standardized data group by converting concentrations of a plurality of gas species dissolved in an insulating oil taken from a determination target oil-filled electric apparatus into ratios;

second standardized data group storage means for storing the standardized data group generated by the second standardized data group generation means;

second discretized data group generation means for generating, on the basis of the standardized data group of the determination target apparatus, the standardized data group being stored in the second standardized data group storage means, a discretized data group by converting the ratios of the concentrations of the gas species, the ratios constituting the standardized data group, into a plurality of discretized attributes using the same predetermined thresholds as in the abnormality cases, the predetermined thresholds being set for the respective gas species;

second discretized data group storage means for storing the discretized data group generated by the second discretized data group generation means; and abnormality determination means for determining a type of an internal abnormality of the determination target apparatus by using the discretized data group of the determination target apparatus, the discretized data group being stored in the second discretized data group storage means, and the decision tree stored in the decision tree storage means.

[Mathematical 5]

$$G(X) = \frac{M(D) - E(X)}{S(X)} \quad \text{Formula (1)}$$

[Mathematical 6]

$$M(D) = \sum_{i=l}^{n} \left[ -\frac{C_i}{|D|} \log_2 \frac{C_i}{|D|} \right] \quad \text{Formula (2)}$$

[Mathematical 7]

$$E(X) = \sum_{j=l}^{v} \left[ \frac{\alpha_j}{|D|} \sum_{k=l}^{m} \left[ -\frac{\beta_{jk}}{\alpha_j} \log_2 \frac{\beta_{jk}}{\alpha_j} \right] \right] \quad \text{Formula (3)}$$

[Mathematical 8]

$$S(X) = \sum_{j=l}^{v} \left[ -\frac{\alpha_j}{|D|} \log_2 \frac{\alpha_j}{|D|} \right] \quad \text{Formula (4)}$$

X: a gas species dissolved in an insulating oil
D: a set of abnormality case data mapped to a node
|D|: the number of pieces of abnormality case data mapped to a node
$C_i$: the number of the i-th type of internal abnormalities in a set D
$\alpha_j$: the number of pieces of abnormality case data at the j-th branch of a gas species X
$\beta_{jk}$: the number of the k-th type of internal abnormalities at the j-th branch of a gas species X
G (X): a gain ratio
M (D): the amount of expected information with respect to the type of the internal abnormality in a set D
E (X): the amount of expected information after classification by a gas species X
S (X): the amount of expected information with respect to a gas species X in a set D
l: the type or a number of a discretized attribute of the first internal abnormality in a set D
m, n: the total number of types of internal abnormalities in a set D
v: the total number of discretized attributes Further, the present invention constructs an abnormality diagnosis program of an oil-filled electric apparatus in which an internal abnormality of an oil-filled electric apparatus is diagnosed using a computer, the program causing a computer to execute the steps of:

generating, on the basis of historical abnormality case data of an oil-filled electric apparatus, the historical abnormality case data being stored in performance data storage means, a standardized data group by converting concentrations of a plurality of gas species dissolved in an insulating oil in the oil-filled electric apparatus into ratios for each of abnormality cases, and storing the standardized data group in first standardized data group storage means;

generating, on the basis of the standardized data group of each of the abnormality cases, the standardized data group being stored in the first standardized data group storage means, a discretized data group by converting the ratios of the concentrations of the gas species, the ratios constituting the standardized data group, into a plurality of discretized attributes using predetermined thresholds set for the respective gas species, and storing the discretized data group in first discretized data group storage means;

generating a decision tree for determining a type of an internal abnormality of an oil-filled electric apparatus by analysis using the following formulae (1) to (4) on the basis of the discretized data group of each of the abnormality cases, the discretized data group being stored in the first discretized data group storage means, and storing the decision tree in decision tree storage means;

generating a standardized data group by converting concentrations of a plurality of gas species dissolved in an insulating oil taken from a determination target oil-filled electric apparatus into ratios, and storing the standardized data group in second standardized data group storage means;

generating, on the basis of the standardized data group of the determination target apparatus, the standardized data group being stored in the second standardized data group storage means, a discretized data group by converting the ratios of the concentrations of the gas species, the ratios constituting the standardized data group, into a plurality of discretized attributes using the same predetermined thresholds as in the abnormality cases, the predetermined thresholds being set for the respective gas species, and storing the discretized data group in second discretized data group storage means; and determining a type of an internal abnormality of the determination target apparatus by using the discretized data group of the determination target apparatus, the discretized data group being stored in the second discretized data group storage means, and the decision tree stored in the decision tree storage means.

[Mathematical 9]

$$G(X) = \frac{M(D) - E(X)}{S(X)} \quad \text{Formula (1)}$$

[Mathematical 10]

$$M(D) = \sum_{i=l}^{n} \left[ -\frac{C_i}{|D|} \log_2 \frac{C_i}{|D|} \right] \quad \text{Formula (2)}$$

[Mathematical 11]

$$E(X) = \sum_{j=l}^{v} \left[ \frac{\alpha_j}{|D|} \sum_{k=l}^{m} \left[ -\frac{\beta_{jk}}{\alpha_j} \log_2 \frac{\beta_{jk}}{\alpha_j} \right] \right] \quad \text{Formula (3)}$$

[Mathematical 12]

$$S(X) = \sum_{j=l}^{v} \left[ -\frac{\alpha_j}{|D|} \log_2 \frac{\alpha_j}{|D|} \right] \quad \text{Formula (4)}$$

X: a gas species dissolved in an insulating oil
D: a set of abnormality case data mapped to a node
|D|: the number of pieces of abnormality case data mapped to a node
$C_i$: the number of the i-th type of internal abnormalities in a set D
$\alpha_j$: the number of pieces of abnormality case data at the j-th branch of a gas species X
$\beta_{jk}$: the number of the k-th type of internal abnormalities at the j-th branch of a gas species X
G (X): a gain ratio
M (D): the amount of expected information with respect to the type of the internal abnormality in a set D
E (X): the amount of expected information after classification by a gas species X
S (X): the amount of expected information with respect to a gas species X in a set D l: the type or a number of a discretized attribute of the first internal abnormality in a set D m, n: the total number of types of internal abnormalities in a set D v: the total number of discretized attributes Further, the present invention constructs a decision tree generation method for generating a decision tree for determining a type of an internal abnormality of an oil-filled electric apparatus using a computer, the method comprising the steps, by a computer, of:

generating, on the basis of historical abnormality case data of an oil-filled electric apparatus, the historical abnormality case data being stored in performance data storage means, a standardized data group by converting concentrations of a plurality of gas species dissolved in an insulating oil in the oil-filled electric apparatus into ratios for each of abnormality cases, and storing the standardized data group in first standardized data group storage means;

generating, on the basis of the standardized data group of each of the abnormality cases, the standardized data group being stored in the first standardized data group storage means, a discretized data group by converting the ratios of the concentrations of the gas species, the ratios constituting the standardized data group, into a plurality of discretized attributes using predetermined thresholds set for the respective gas species, and storing the discretized data group in first discretized data group storage means; and generating a decision tree for determining a type of an internal abnormality of an oil-filled electric apparatus by analysis using the following formulae (1) to (4) on the basis of the discretized data group of each of the abnormality cases, the discretized data group being stored in the first discretized data group storage means.

[Mathematical 13]

$$G(X) = \frac{M(D) - E(X)}{S(X)} \quad \text{Formula (1)}$$

[Mathematical 14]

$$M(D) = \sum_{i=l}^{n} \left[ -\frac{C_i}{|D|} \log_2 \frac{C_i}{|D|} \right] \quad \text{Formula (2)}$$

[Mathematical 15]

$$E(X) = \sum_{j=l}^{v} \left[ \frac{\alpha_j}{|D|} \sum_{k=l}^{m} \left[ -\frac{\beta_{jk}}{\alpha_j} \log_2 \frac{\beta_{jk}}{\alpha_j} \right] \right] \quad \text{Formula (3)}$$

[Mathematical 16]

$$S(X) = \sum_{j=l}^{v} \left[ -\frac{\alpha_j}{|D|} \log_2 \frac{\alpha_j}{|D|} \right] \quad \text{Formula (4)}$$

X: a gas species dissolved in an insulating oil

D: a set of abnormality case data mapped to a node

|D|: the number of pieces of abnormality case data mapped to a node $C_i$: the number of the i-th type of internal abnormalities in a set D $\alpha_j$: the number of pieces of abnormality case data at the j-th branch of a gas species X $\beta_{jk}$: the number of the k-th type of internal abnormalities at the j-th branch of a gas species X G (X): a gain ratio M (D): the amount of expected information with respect to the type of the internal abnormality in a set D E (X): the amount of expected information after classification by a gas species X S (X): the amount of expected information with respect to a gas species X in a set D l: the type or a number of a discretized attribute of the first internal abnormality in a set D m, n: the total number of types of internal abnormalities in a set D v: the total number of discretized attributes Further, the present invention constructs a decision tree generation program for generating a decision tree for determining a type of an internal abnormality of an oil-filled electric apparatus using a computer, the program causing a computer to execute the steps of:

generating, on the basis of historical abnormality case data of an oil-filled electric apparatus, the historical abnormality case data being stored in performance data storage means, a standardized data group by converting concentrations of a plurality of gas species dissolved in an insulating oil in the oil-filled electric apparatus into ratios for each of abnormality cases, and storing the standardized data group in first standardized data group storage means;

generating, on the basis of the standardized data group of each of the abnormality cases, the standardized data group being stored in the first standardized data group storage means, a discretized data group by converting the ratios of the concentrations of the gas species, the ratios constituting the standardized data group, into a plurality of discretized attributes using predetermined thresholds set for the respective gas species, and storing the discretized data group in first discretized data group storage means; and generating a decision tree for determining a type of an internal abnormality of an oil-filled electric apparatus by analysis using the following formulae (1) to (4) on the basis of the discretized data group of each of the abnormality cases, the discretized data group being stored in the first discretized data group storage means.

[Mathematical 17]

$$G(X) = \frac{M(D) - E(X)}{S(X)} \quad \text{Formula (1)}$$

[Mathematical 18]

$$M(D) = \sum_{i=l}^{n} \left[ -\frac{C_i}{|D|} \log_2 \frac{C_i}{|D|} \right] \quad \text{Formula (2)}$$

[Mathematical 19]

$$E(X) = \sum_{j=l}^{v} \left[ \frac{\alpha_j}{|D|} \sum_{k=l}^{m} \left[ -\frac{\beta_{jk}}{\alpha_j} \log_2 \frac{\beta_{jk}}{\alpha_j} \right] \right] \quad \text{Formula (3)}$$

[Mathematical 20]

$$S(X) = \sum_{j=l}^{v} \left[ -\frac{\alpha_j}{|D|} \log_2 \frac{\alpha_j}{|D|} \right] \quad \text{Formula (4)}$$

X: a gas species dissolved in an insulating oil

D: a set of abnormality case data mapped to a node

|D|: the number of pieces of abnormality case data mapped to a node $C_i$: the number of the i-th type of internal abnormalities in a set D α_j: the number of pieces of abnormality case data at the j-th branch of a gas species X β_{jk}: the number of the k-th type of internal abnormalities at the j-th branch of a gas species X G (X): a gain ratio M (D): the amount of expected information with respect to the type of the internal abnormality in a set D E (X): the amount of expected information after classification by a gas species X S (X): the amount of expected information with respect to a gas species X in a set D l: the type or a number of a discretized attribute of the first internal abnormality in a set D m, n: the total number of types of internal abnormalities in a set D v: the total number of discretized attributes Further, the present invention constructs an abnormality diagnosis method of an oil-filled electric apparatus in which an internal abnormality of an oil-filled electric apparatus is diagnosed using a computer, the method comprising the steps, by a computer, of:

generating, on the basis of historical abnormality case data of an oil-filled electric apparatus, the historical abnormality case data being stored in performance data storage means, a standardized data group by converting concentrations of a plurality of gas species dissolved in an insulating oil in the oil-filled electric apparatus into ratios for each of abnormality cases, and storing the standardized data group in first standardized data group storage means;

calculating, on the basis of the standardized data group of each of the abnormality cases, the standardized data group being stored in the first standardized data group storage means, certainty factors corresponding to the respective ratios of the concentrations of the respective gas species, the ratios constituting the standardized data group, using predetermined membership functions set for the respective gas species, generating a discretized data group by converting the ratios of the concentrations of the gas species into a plurality of discretized attributes on the basis of the certainty factors, and storing the discretized data group in first discretized data group storage means;

generating a decision tree for determining a type of an internal abnormality of an oil-filled electric apparatus by analysis using the following formulae (5) to (8) on the basis of the discretized data group of each of the abnormality cases, the discretized data group being stored in the first discretized data group storage means, and storing the decision tree in decision tree storage means;

generating a standardized data group by converting concentrations of a plurality of gas species dissolved in an insulating oil taken from a determination target oil-filled electric apparatus into ratios, and storing the standardized data group in second standardized data group storage means;

generating, on the basis of the standardized data group of the determination target apparatus, the standardized data group being stored in the second standardized data group storage means, a discretized data group by converting the ratios of the concentrations of the gas species, the ratios constituting the standardized data group, into a plurality of discretized attributes on the basis of the same predetermined certainty factors as in the abnormality cases, the predetermined certainty factors being set for the respective gas species, and storing the discretized data group in second discretized data group storage means; and determining a type of an internal abnormality of the determination target apparatus by using the discretized data group of the determination target apparatus, the discretized data group being stored in the second discretized data group storage means, and the decision tree stored in the decision tree storage means.

[Mathematical 21]

$$G'(X) = \frac{M'(D') - E'(X)}{S'(X)}$$ Formula (5)

[Mathematical 22]

$$M'(D') = \sum_{i=l}^{n} \left[ -\frac{C'_i}{|D'|} \log_2 \frac{C'_i}{|D'|} \right]$$ Formula (6)

[Mathematical 23]

$$E'(X) = \sum_{j=l}^{v} \left[ \frac{\alpha'_j}{|D'|} \sum_{k=l}^{m} \left[ -\frac{\beta'_{jk}}{\alpha'_j} \log_2 \frac{\beta'_{jk}}{\alpha'_j} \right] \right]$$ Formula (7)

[Mathematical 24]

$$S'(X) = \sum_{j=l}^{v} \left[ -\frac{\alpha'_j}{|D'|} \log_2 \frac{\alpha'_j}{|D'|} \right]$$ Formula (8)

X: a gas species dissolved in an insulating oil

D': a set of abnormality case data mapped to a node and based on a certainty factor

|D'|: the sum of certainty factors of abnormality case data mapped to a node $C_i'$: the sum of certainty factors of the i-th type of internal abnormalities in a set D'

$\alpha_j'$: the sum of certainty factors of abnormality case data at the j-th branch of a gas species X $\beta_{jk}'$: the sum of certainty factors of the k-th type of internal abnormalities at the j-th branch of a gas species X G' (X): a gain ratio M' (D'): the amount of expected information with respect to the type of the internal abnormality in a set D'

E' (X): the amount of expected information after classification by a gas species X S' (X): the amount of expected information with respect to the gas species X in the set D' l: the type or a number of a discretized attribute of the first internal abnormality in the set D m, n: the total number of types of internal abnormalities in the set D v: the total number of the discretized attributes Further, the present invention constructs an abnormality predictive diagnosis method of an oil-filled electric apparatus in which an internal abnormality of an oil-filled electric apparatus is predictively diagnosed using a computer, the method comprising the steps, by a computer, of:

generating, on the basis of historical abnormality case data of an oil-filled electric apparatus, the historical abnormality case data being stored in performance data storage means, a standardized data group by converting concentrations of a plurality of gas species dissolved in an insulating oil in the oil-filled electric apparatus into ratios for each of abnormality cases, and storing the standardized data group in first standardized data group storage means;

generating, on the basis of the standardized data group of each of the abnormality cases, the standardized data group being stored in the first standardized data group storage means, a discretized data group by converting the ratios of the concentrations of the gas species, the ratios constituting the standardized data group, into a plurality of discretized attributes using predetermined thresholds set for the respective gas species, and storing the discretized data group in first discretized data group storage means;

generating a decision tree for determining a type of an internal abnormality of an oil-filled electric apparatus by analysis using the following formulae (1) to (4) on the basis of the discretized data group of each of the abnormality cases, the discretized data group being stored in the first discretized data group storage means, and storing the decision tree in decision tree storage means;

calculating, with respect to a time series data group of gas concentration, the data group being extracted for each of a plurality of gas species dissolved in an insulation oil in a determination target oil-filled electric apparatus on the basis of three or more pieces of historical performance data of the determination target oil-filled electric apparatus, the performance data being stored in the performance data storage means, a first regression line, dispersion of the time series data group with respect to the first regression line, and uncertainty based on the dispersion, and storing the first regression line, the dispersion and the uncertainty in first regression line data storage means;

calculating, with respect to the latest three or more pieces of the performance data in the time series data group extracted on the basis of the performance data stored in the performance data storage means, a second regression line and a first predicted gas concentration as a gas concentration at a time when a predetermined period of time has passed from the latest measurement time on the second regression line, and storing the second regression line and the first predicted gas concentration in second regression line data storage means;

calculating the sum of the uncertainty stored in the first regression line data storage means and the first predicted gas concentration stored in the second regression line data storage means as a second predicted gas concentration, generating a predicted time series data group composed of the second predicted gas concentration and the latest piece of the performance data in the time series data group extracted on the basis of the performance data stored in the performance data storage means, generating a third regression line with respect to the predicted time series data group, and storing the third regression line in third regression line data storage means;

extracting a third predicted gas concentration at the same time on the third regression line with respect to the third regression line of each of the gas species, the third regression line being stored in the third regression line data storage means, generating a standardized data group by converting third predicted gas concentrations of the gas species into ratios, and storing the standardized data group in second standardized data group storage means;

generating, on the basis of the standardized data group of the determination target apparatus, the standardized data group being stored in the second standardized data group storage means, a discretized data group by converting the ratios of the third predicted gas concentrations of the gas species, the ratios constituting the standardized data group, into a plurality of discretized attributes using the same predetermined thresholds as in the abnormality cases, the predetermined thresholds being set for the respective gas species, and storing the discretized data group in second discretized data group storage means; and determining a type of an internal abnormality of the determination target apparatus by using the discretized data group of the determination target apparatus, the discretized data group being stored in the second discretized data group storage means, and the decision tree stored in the decision tree storage means.

[Mathematical 25]

$$G(X) = \frac{M(D) - E(X)}{S(X)} \quad \text{Formula (1)}$$

[Mathematical 26]

$$M(D) = \sum_{i=l}^{n} \left[ -\frac{C_i}{|D|} \log_2 \frac{C_i}{|D|} \right] \quad \text{Formula (2)}$$

[Mathematical 27]

$$E(X) = \sum_{j=l}^{v} \left[ \frac{\alpha_j}{|D|} \sum_{k=l}^{m} \left[ -\frac{\beta_{jk}}{\alpha_j} \log_2 \frac{\beta_{jk}}{\alpha_j} \right] \right] \quad \text{Formula (3)}$$

[Mathematical 28]

$$S(X) = \sum_{j=l}^{v} \left[ -\frac{\alpha_j}{|D|} \log_2 \frac{\alpha_j}{|D|} \right] \quad \text{Formula (4)}$$

X: a gas species dissolved in an insulating oil
D: a set of abnormality case data mapped to a node
|D|: the number of pieces of abnormality case data mapped to a node
$C_i$: the number of the i-th type of internal abnormalities in a set D
$\alpha_j$: the number of pieces of abnormality case data at the j-th branch of a gas species X
$\beta_{jk}$: the number of the k-th type of internal abnormalities at the j-th branch of a gas species X
G (X): a gain ratio
M (D): the amount of expected information with respect to the type of the internal abnormality in a set D
E (X): the amount of expected information after classification by a gas species X
S (X): the amount of expected information with respect to a gas species X in a set D
l: the type or a number of a discretized attribute of the first internal abnormality in a set D
m, n: the total number of types of internal abnormalities in a set D
v: the total number of discretized attributes Advantageous Effects of Invention The abnormality diagnosis method of an oil-filled electric apparatus according to the present invention as above can analyze historical abnormality case data with high accuracy by employing a method for generating a decision tree on the basis of the discretized data on which specific data processing is performed. Therefore, the abnormality diagnosis method according to the present invention has a diagnostic accuracy equal to or higher than that of a diagnostic specialist having reached a certain level and is highly effective as diagnosis using a machine in a method of analysis utilizing gas concentration in oil.

Further, it can be expected that the abnormality predictive diagnosis method of an oil-filled electric apparatus according to the present invention performs predictive diagnosis of an internal abnormality which may occur in the future with high accuracy by employing the specific decision tree generation method with respect to the predicted concentrations of the respective gas species which are predicted using the specific regression lines to thereby determine the type of the internal abnormality of the determination target apparatus.

BRIEF DESCRIPTION OF THE DRAWINGS

FIG. 8 is a diagram virtually illustrating, as a list, a part of abnormality case data extracted in the present invention.

FIG. 9 is a diagram virtually illustrating, as a list, a part of a standardized data group which is generated by converting concentrations of a plurality of gas species dissolved in an insulating oil in an oil-filled electric apparatus into ratios for each abnormality case by dividing a concentration of each of the gas species in FIG. 8 by the sum of the concentrations of all of the gas species measured for each abnormality case.

FIG. 10 is a diagram virtually illustrating, as a list, a part of a discretized data group which is generated by converting the concentration ratios of the standardized data group shown in FIG. 9 into a plurality of discretized attributes using predetermined thresholds which are set for the respective gas species.

FIG. 11 is a diagram in which, with respect to a certain gas species (X), the numbers of respective five types of internal abnormalities corresponding to respective three types of discretized attributes, the total numbers of the respective internal abnormalities, and the total numbers of all of the internal abnormalities at the respective discretized attributes are compiled.

FIG. 15 is a diagram illustrating a part of discretized data generated using membership functions regarding data of a certain abnormality case.

DESCRIPTION OF EMBODIMENTS

Next, embodiments of the present invention will be described in detail on the basis of the appended drawings.

First Embodiment

Figure 1:
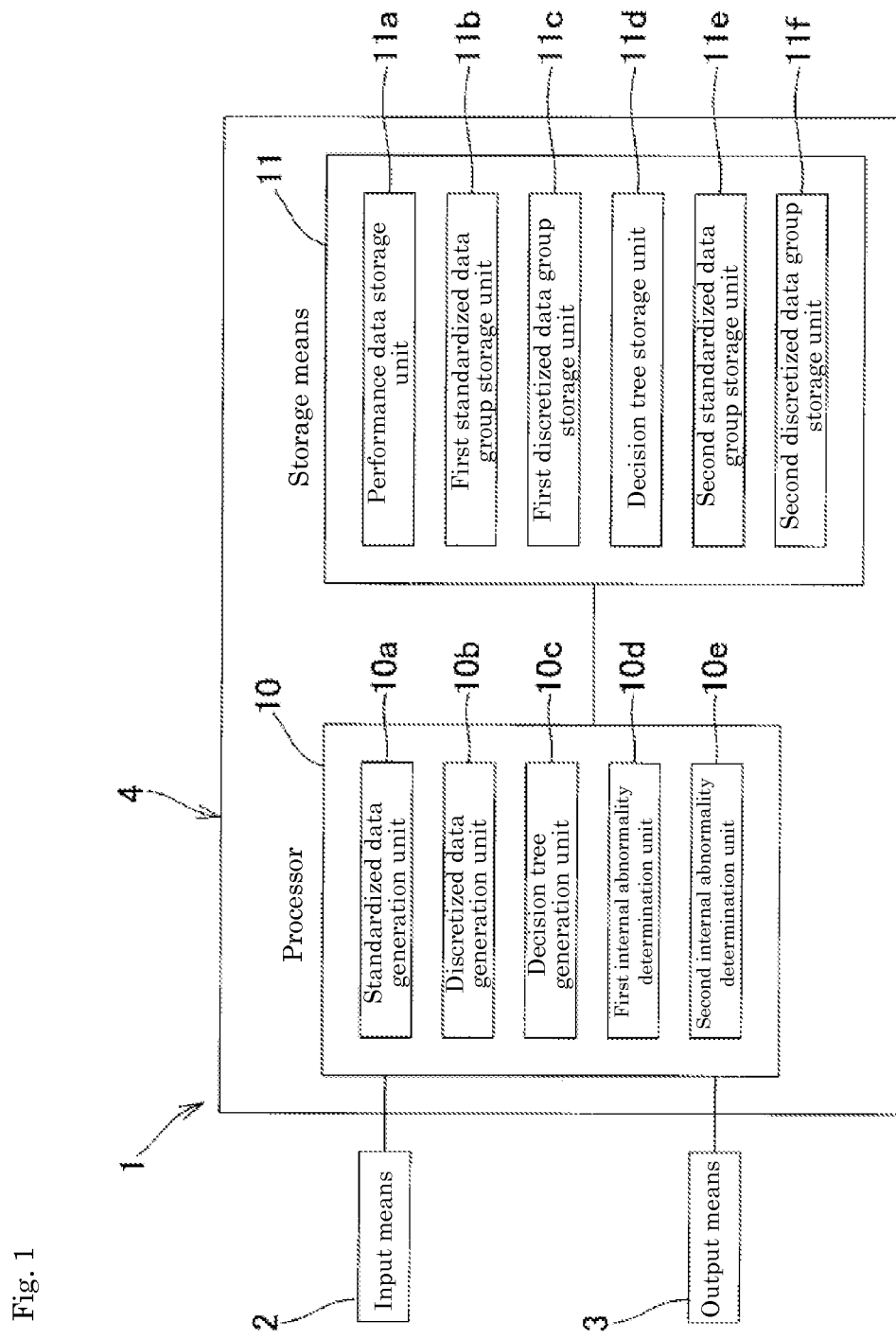
FIG. 1 is a block diagram illustrating a main configuration of a representative abnormality diagnosis system for performing an abnormality diagnosis method of an oil-filled electric apparatus in a first embodiment of the present invention.

FIG. 1 is a block diagram illustrating a main configuration of a representative abnormality diagnosis system for performing an abnormality diagnosis method of an oil-filled electric apparatus in a first embodiment of the present invention. As shown in FIG. 1, an abnormality diagnosis system 1 is provided with input means 2, output means 3, and a computer 4. The computer 4 is provided with a processor 10 and storage means 11. The processor 10 is mainly composed of a microprocessor, and includes a storage unit (not shown) which is composed of RAM and ROM. In the processor 10, programs which define procedures for various general processing operations and a procedure for executing a later-described diagnosis method of the present invention and the like and processing data are stored.

The processor 10 is provided with a standardized data generation unit 10a, a discretized data generation unit 10b, a decision tree generation unit 10c, a first internal abnormality determination unit 10d, and a second internal abnormality determination unit 10e.

The standardized data generation unit 10a has a function to generate, on the basis of historical abnormality case data of an oil-filled electric apparatus, the data being stored in a performance data storage unit 11a, a standardized data group by converting concentrations of a plurality of gas species dissolved in an insulating oil in the oil-filled electric apparatus into ratios for each abnormality case, and store the thus generated standardized data group in a first standardized data group storage unit 11b. Further, the standardized data generation unit 10a also has a function to generate a standardized data group by converting concentrations of a plurality of gas species dissolved in an insulating oil which is taken from the determination target oil-filled electric apparatus into ratios, and store the thus generated standardized data group in a second standardized data group storage unit 11e. Further, the concentrations of the gas species dissolved in the insulating oil which is taken from the determination target oil-filled electric apparatus may be stored in the performance data storage unit 11a, or may also be input by the input means 2.

The discretized data generation unit 10b has a function to generate, on the basis of the standardized data group of each abnormality case, the data group being stored in the first standardized data group storage unit 11b, a discretized data group by converting the concentration ratios of the gas species, the concentration ratios constituting the standardized data group of each abnormality case, into a plurality of discretized attributes using predetermined thresholds which are set for the respective gas species, and store the thus generated discretized data group in a first discretized data group storage unit 11c. Further, the discretized data generation unit 10b also has a function to generate, on the basis of the standardized data group of the determination target apparatus, the data group being stored in the second standardized data group storage unit 11e, a discretized data group by converting the concentration ratios of the gas species, the concentration ratios constituting the standardized data group of the determination target apparatus, into a plurality of discretized attributes using the predetermined thresholds as in the abnormality cases which are set for the respective gas species, and store the thus generated discretized data group in a second discretized data group storage unit 11f.

The decision tree generation unit 10c has a function to generate a decision tree for determining the type of the internal abnormality of the oil-filled electric apparatus by analysis using the above formulae (1) to (4) on the basis of the discretized data group of each abnormality case, the discretized data group being stored in the first discretized data group storage unit 11c, and store the thus generated decision tree in a decision tree storage unit 11d.

The first internal abnormality determination unit 10d which is an optional configuration has a function to determine as to whether or not the concentrations of the gas species dissolved in the insulating oil which is taken from the determination target oil-filled electric apparatus fall within respective predetermined normal ranges.

The second internal abnormality determination unit 10e has a function to determine the type of the internal abnormality of the determination target apparatus by using the discretized data group of the determination target apparatus, the discretized data group being stored in the second discretized data group storage unit 11f, and the decision tree which is stored in the decision tree storage means 11d.

Further, a result of the determination may be stored in the storage means 11, or may also be output by the output means 3.

The storage means 11 is provided with the performance data storage unit 11a, the first standardized data group storage unit 11b, the first discretized data group storage unit 11c, the decision tree storage unit 11d, the second standardized data group storage unit 11e, and the second discretized data group storage unit 11f. Further, although not shown in the drawings, the storage means 11 may be provided with a result storage unit which stores a result of the diagnosis.

In the performance data storage unit 11a, measured data of concentrations of a plurality of gas species dissolved in an insulating oil in the oil-filled electric apparatus in the past may be stored. In this case, since measured data at a normal time are also contained in the performance data along with the historical abnormality case data, the measured data are stored so as to be distinguished between abnormality case data or not. Further, in view of further improvement in accuracy of the diagnosis, it is desirable to add abnormality case data which is newly obtained to the historical abnormality case data so as to increase the total number of abnormality cases.

In the first standardized data group storage unit 11b, the standardized data group which has been generated in the standardized data generation unit 10a on the basis of the historical abnormality case data is stored. In the first discretized data group storage unit 11c, the discretized data group which has been generated in the discretized data generation unit 10b on the basis of the standardized data group stored in the first standardized data group storage unit 11b is stored. In the decision tree storage unit 11d, the decision tree which has been generated in the decision tree generation unit 10d is stored. In the second standardized data group storage unit 11e, the standardized data group which has been generated in the standardized data generation unit 10a on the basis of the concentrations of the plurality of gas species dissolved in the insulating oil which is taken from the determination target oil-filled electric apparatus is stored. In the second discretized data group storage unit 11f, the discretized data group which has been generated in the discretized data generation unit 10b on the basis of the second standardized data group storage unit 11d is stored.

In the present embodiment, an example in which a single computer constitutes the diagnosis system has been shown. However, the diagnosis system may be configured in such a manner that a computer that has a configuration required for generating a decision tree is used as a host computer, the host computer is connected to another computer that can be used in a place where the determination target oil-filled electric apparatus is located through a communication circuit such as internet, and the performance data of the determination target oil-filled electric apparatus is managed by the separate computer.

The functions described above are achieved by programs which define procedures for various processing operations, and are stored in the storage unit (not shown) which is provided in the processor 10 and composed of RAM and ROM.

Next, a processing procedure in the abnormality diagnosis system according to the present invention will be described on the basis of an embodiment.

Figure 3:
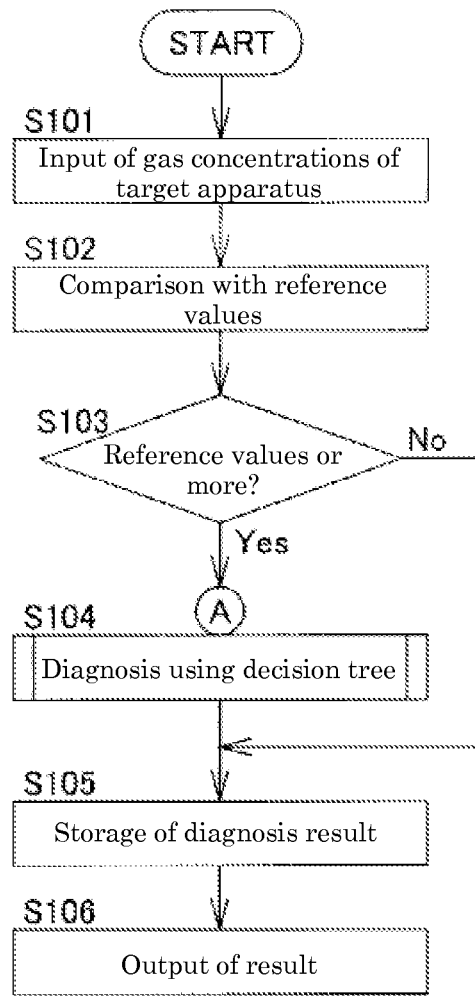
FIG. 3 is a schematic flow chart illustrating a flow from input of concentrations of a plurality of gas species dissolved in an insulating oil which is taken from the determination target oil-filled electric apparatus until obtaining a result of abnormality diagnosis.

FIG. 3 is a schematic flow chart illustrating a flow from input of concentrations of a plurality of gas species dissolved in an insulating oil which is taken from the determination target oil-filled electric apparatus until obtaining a result of abnormality diagnosis.

When concentrations of a plurality of gas species dissolved in an insulating oil which is taken from the determination target oil-filled electric apparatus are input by the input means 3 or by selecting from the performance data storage unit 11a (step S101), the computer 4 determines as to whether or not the concentrations of the gas species fall within respective predetermined normal ranges, that is, as to whether or not the concentrations of the gas species are equal to or more than respective reference values which are previously determined for the respective gas species (steps S102 and S103). When none of the gas concentrations is equal to or more than the corresponding reference value, a result of the diagnosis indicating that there is no abnormality is stored in the result storage unit (not shown) of the storage means 11 (step S105), and if necessary, the result of the diagnosis is output by the output means 3 (step S106). On the other hand, when there is a gas concentration that is equal to or more than the corresponding reference value, diagnosis using a decision tree is performed (step S104), a result of the diagnosis using the decision tree is stored also in the result storage unit (step S105), and if necessary, the result of the diagnosis is output by the output means 3 (step S106).

Further, steps S102 and S103 are optional configurations. For example, when it is already known that the concentration of a certain gas species is equal to or more than its reference value, these steps are not necessary. Therefore, in such a case, these steps may be omitted in the first internal abnormality determination unit 10d.

Figure 4:
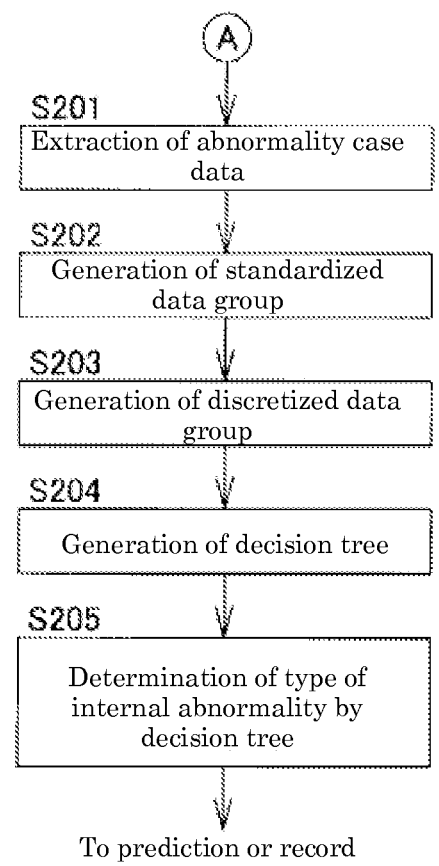
FIG. 4 is schematic flow chart illustrating details of a step of diagnosis using a decision tree in FIG. 3 (step S104).

FIG. 4 is schematic flow chart illustrating details of a step of the diagnosis using the decision tree in FIG. 3 (step S104).

In step S104, abnormality case data is first extracted from historical performance data of the oil-filled electric apparatus, the historical performance data being stored in the performance data storage unit 11a, in the standardized data generation unit 10a (step S201), and, on the basis of the abnormality case data, a standardized data group is generated by converting concentrations of a plurality of gas species dissolved in the insulating oil of the oil-filled electric apparatus into ratios for each abnormality case and the thus generated standardized data group is stored in the first standardized data group storage unit 11b (step S202).

Further, by performing the same process as above, the concentrations of the gas species dissolved in the insulation oil which is taken from the determination target oil-filled electric apparatus (hereinafter, also referred to as "determination target gases"), the concentrations being input in step S101, are converted into ratios to thereby generate a standardized data group, and the thus generated standardized data group is stored in the second standardized data group storage unit 11e (step S202).

Converting the data which is represented as the gas concentrations for each case into the ratios thereof in this manner makes it possible to generate a decision tree that takes into account a relative relationship among the gas species. Such a relative relationship among gas species is considered also in determination by a skilled diagnostic specialist. Therefore, by employing such a series of steps, a decision tree that is based on the same determination criterion as that in a determination method by a skilled diagnostic specialist is generated, thereby making it possible to realize a diagnosis method that has further improved diagnostic accuracy.

Here, the processing of the historical abnormality case data will be described in detail. As shown in FIG. 8, for example, with respect to data of respective abnormality cases (Case 1, Case 2, . . . ), concentrations (ppm) (Case 1: $a_{11}, a_{12}, \ldots$, Case 2: $a_{21}, a_{22}, \ldots$) of respective gas species (Gas 1, Gas 2, Gas 3, Gas 4, Gas 5, . . . ), the sum of the measured concentrations of all of the gas species (Case 1: $\Sigma a_{1p} = a_{11} + a_{12} + \ldots$, Case 2: $\Sigma a_{2p} = a_{21} + a_{22} + \ldots, \ldots$), and the type of a representative internal abnormality in the respective cases (Abnormality 1, Abnormality 2, . . . ) are extracted as the abnormality case data from the performance data storage unit 11a. Further, FIG. 8 is a list which is virtually illustrated (step S201).

Further, examples of the gas species include methane, ethane, ethylene, propane, propylene, isobutane, acetylene, hydrogen, carbon monoxide, and normal butane. These gas species are used as indexes in gas analysis of an oil-filled electric apparatus. Among these gas species, representative several types may be selected, or more than several types may also be selected. However, when the number of types of gas species is increased, the diagnostic accuracy tends to be improved.

Further, examples of the type of internal abnormality in the case of, for example, a transformer include abnormality in a tap portion, abnormality in an iron core portion, abnormality in a coil portion, abnormality in a lead portion, and oil leakage from a switch cell. Plural ones of these internal abnormalities may be contained in data of a single abnormality case. In such a case, a representative type of the internal abnormalities is selected as described above. Therefore, the performance data is stored in the performance data storage unit 11a so that the case where a plurality of types of internal abnormalities are contained in a single abnormality case is distinguishable. Further, as will be described later, the type of the internal abnormality that is to be finally determined is decided by taking into account all types of internal abnormalities.

Then, as shown in FIG. 9, for example, the concentration of each of the gas species in FIG. 8 is divided by the sum of the concentrations of all of the gas species (the total, namely, $\Sigma a_{1p}$ in Case 1, $\Sigma a_{2p}$ in Case 2, . . . ), the concentrations being measured for each of the cases, to thereby generate a standardized data group which is obtained by converting the concentrations of the plurality of gas species dissolved in the insulating oil of the oil-filled electric apparatus to ratios for each of the abnormality cases in step S202. Further, FIG. 9 is a list which is virtually illustrated as with FIG. 8.

Then, in the discretized data generation unit 11b, on the basis of the standardized data group of each of the abnormality cases, the data group being stored in the first standardized data group storage unit 11b, a discretized data group is generated by converting the concentration ratios of the gas species, the concentration ratios constituting the standardized data group, into a plurality of discretized attributes using predetermined thresholds which are set for the respective gas species, and the thus generated discretized data group is stored in the first discretized data group storage unit 11c in step S203. Further, on the basis of the standardized data group of the determination target apparatus, the data group being stored in the second standardized data group storage unit 11c, a discretized data group is generated by converting the concentration ratios of the gas species, the concentration ratios constituting the standardized data group, into a plurality of discretized attributes using predetermined thresholds which are set for the respective gas species, and the thus generated discretized data group is stored in the second discretized data group storage unit 11f in step S203. The thresholds used for generating the discretized data group of the respective abnormality cases are the same as the thresholds used for generating the discretized data group of the determination target gases.

Here, the processing of the historical abnormality case data will be specifically described. As shown in FIG. 10, the discretized data group is generated from the standardized data group shown in FIG. 9 by converting the concentration ratios into the plurality of discretized attributes using the predetermined thresholds which are set for the respective gas species (step S203). The number of the discretized attributes is not limited to any specific number. In the present embodiment, as shown in FIG. 10, three discretized attributes including "Extremely Small Amount", "Small Amount" and "Large Amount" which meet the determination criteria of a diagnostic specialist are employed as the discretized attributes. That is, the standardized data which is a continuous attribute is divided into three by two specific large and small thresholds. When a ratio is equal to or smaller than the small threshold, "Extremely Small Amount" is applied thereto. When a ratio is larger than the small threshold as well as equal to or smaller than the large threshold, "Small Amount" is applied thereto. When a ratio is larger than the large threshold, "Large Amount" is applied thereto. When the three attributes which meet the determination criteria of a diagnostic specialist are employed in this manner, the diagnostic accuracy tends to be improved. Further, as the thresholds, values that are empirically determined by a diagnostic specialist for the respective gas species from historical abnormality case data and the like are used. Therefore, when another abnormality case data will be added in the future, the thresholds are determined on the basis of determination which takes this data into consideration in addition to determination on the basis of the historical abnormality case data.

Further, the thresholds may be stored in a storage unit other than the storage units 11a to 11f of the storage means 11, or may also be stored in the first or second discretized data group storage unit.

Next, in step S204, a decision tree for determining the type of the internal abnormality of the oil-filled electric apparatus is generated by analysis using the above-described formulae (1) to (4) in the decision tree generation unit 10c on the basis of the discretized data group of each of the abnormality cases, the discretized data group being stored in the first discretized data group storage unit 11c, and the thus generated decision tree is stored in the decision tree storage unit 11d.

Figure 7:
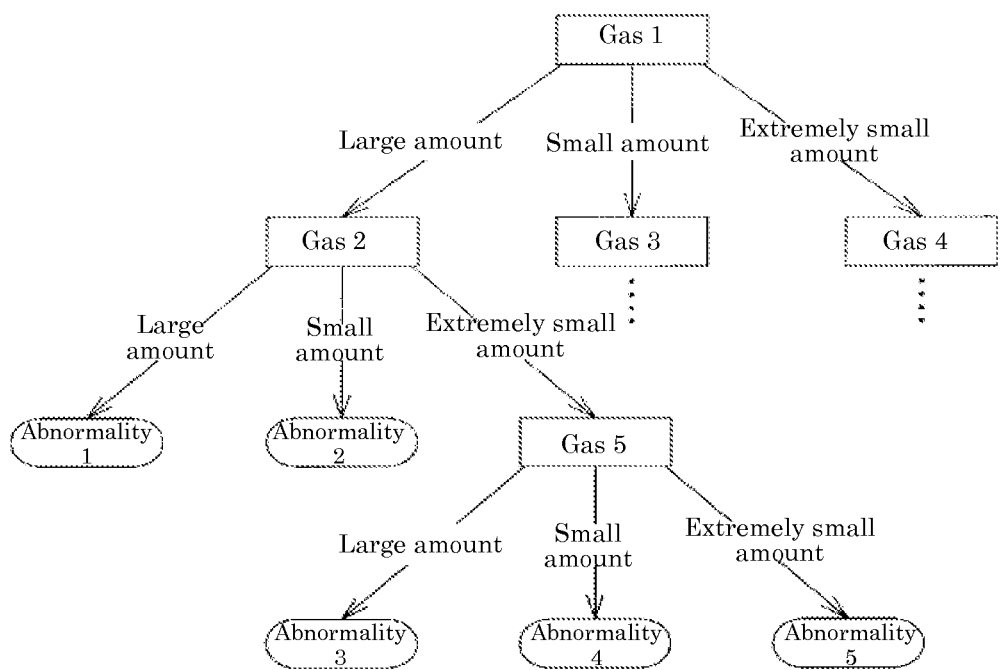
FIG. 7 is a diagram illustrating a part of a tree structure of a decision tree which is generated in the present invention.
Figure 12:
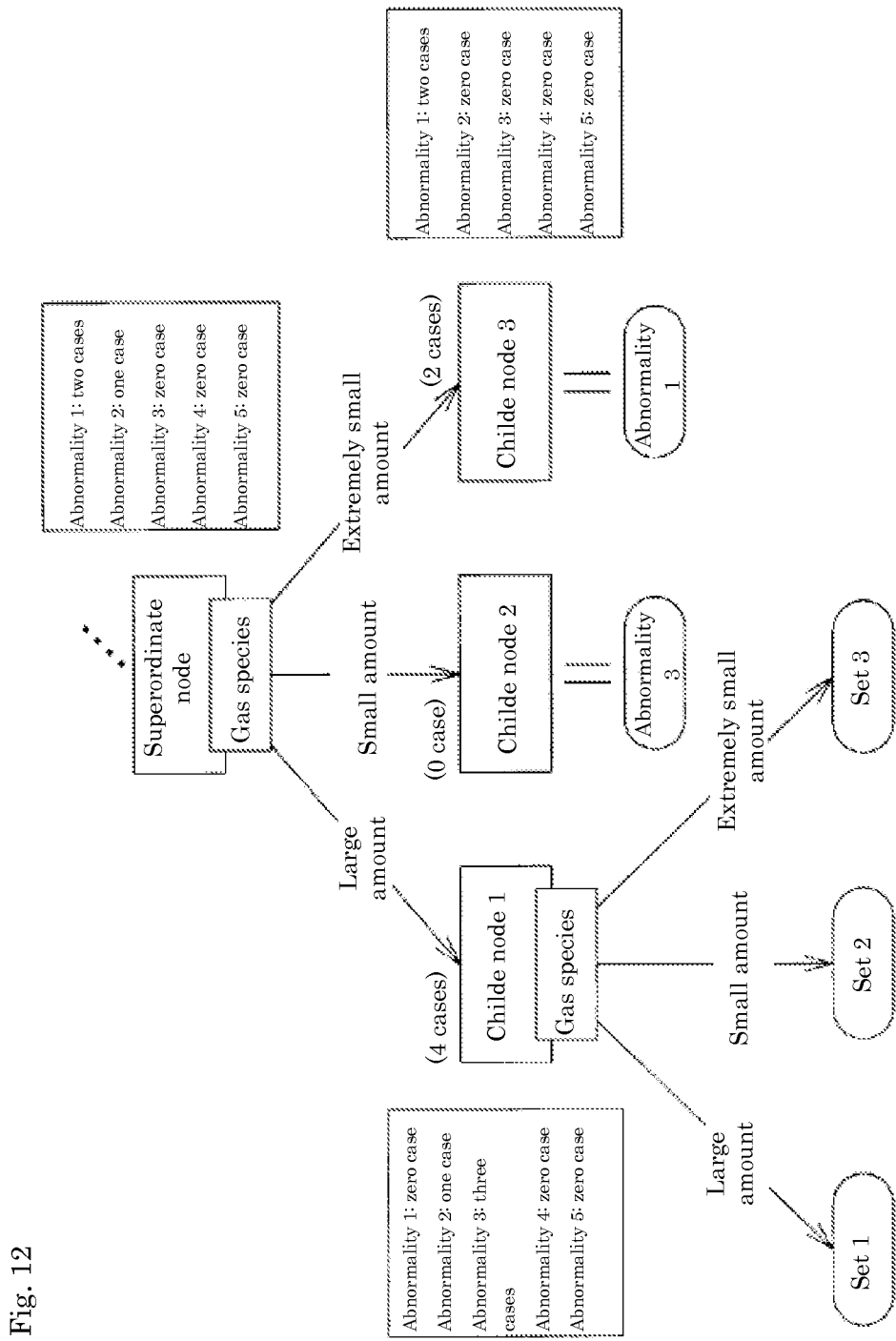
FIG. 12 is an explanatory diagram illustrating procedures of determination of a leaf node and labeling in the course of generation of a decision tree.
Figure 13:
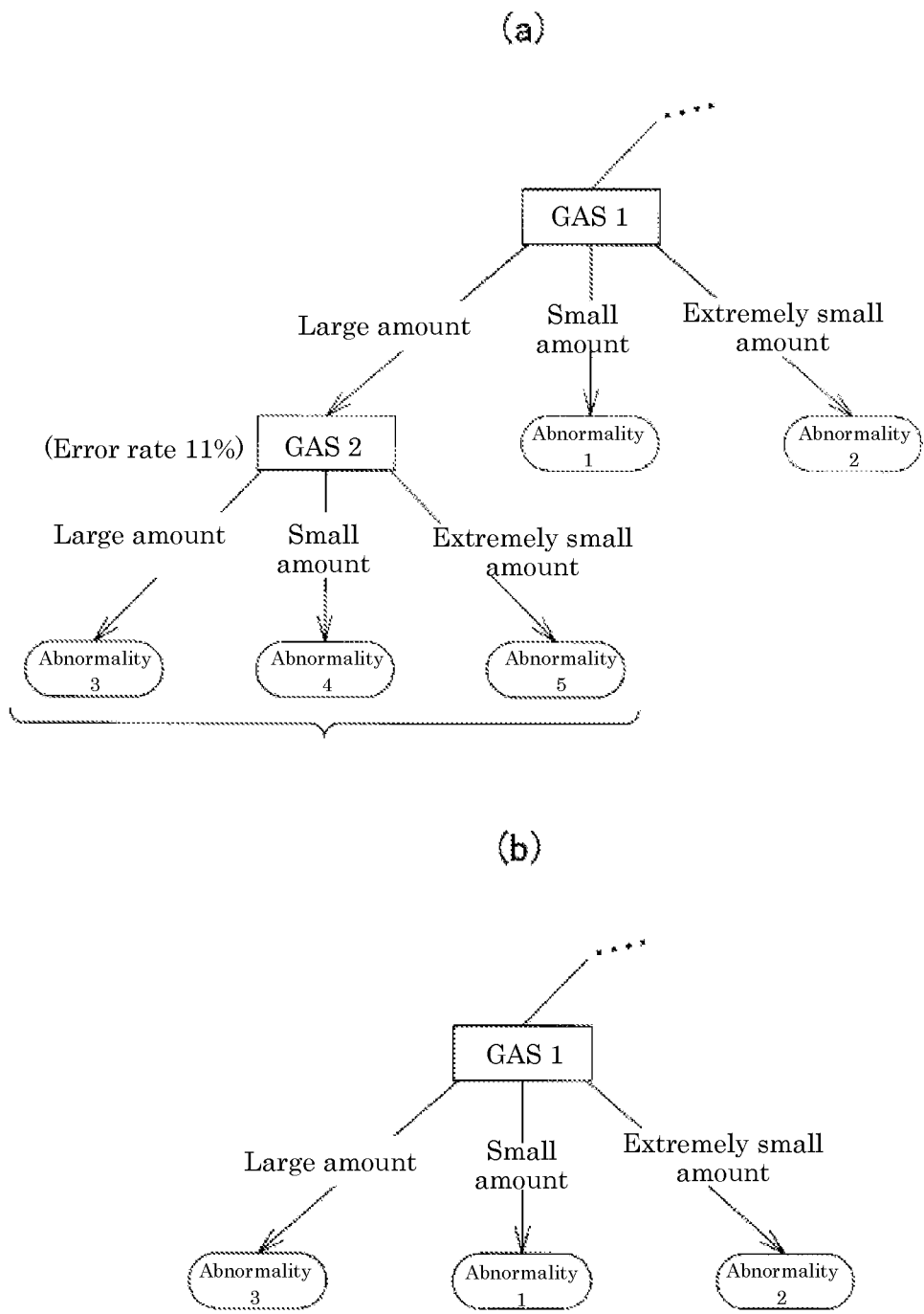
FIG. 13A and FIG. 13B are explanatory diagrams illustrating a procedure of pruning in the course of generation of a decision tree.

A procedure for generating the decision tree by the analysis using the above-described formulae (1) to (4) will be specifically described on the basis of a table shown in FIG. 11 which is determined for each gas species, and diagrams shown in FIGS. 7, 12 and 13 each of which illustrates a part of a decision tree.

FIG. 11 takes an example in which five types of internal abnormalities (Abnormalities 1 to 5) and three discretized attributes (branches) including "Large Amount" (defined as a first branch), "Small Amount" (defined as a second branch) and "Extremely Small Amount" (defined as a third branch) are employed regarding a certain gas species (X), and lists the numbers ($\beta_{11}$ to $\beta_{35}$) of the respective internal abnormalities (Abnormalities 1 to 5) corresponding to the respective discretized attributes, the total numbers ($C_1$ to $C_5$) of the respective internal abnormalities, and the total numbers ($\alpha_1$ to $\alpha_3$) of all of the internal abnormalities at the respective discretized attributes (branches) in the certain gas species (X). Therefore, a table corresponding to FIG. 11 is virtually generated for each gas species.

An analysis procedure is generally as follows.

(i) A node to which all pieces of historical abnormality case data are mapped is generated (the node corresponding to "Gas 1" in FIG. 7). Therefore, a set D of the abnormality case data mapped to this node is all historical abnormality cases, and the number of the all historical abnormality cases is |D|.

(ii) With respect to the set D, a gain ratio G (X) is calculated using the above-described formulae (1) to (4) for each gas species on the basis of the values in the table shown in FIG. 11, the values being generated for each gas species. Then, a gas species (Xmax) having the largest gain ratio G (X) is determined as a test attribute of this node.

(iii) The set D is divided into subsets according to discretized attributes of the gas species Xmax. In a case where the gas species Xmax has characteristics as shown in the table of FIG. 11, the set D is divided into subsets having the respective numbers $\alpha_1$, $\alpha_2$, and $\alpha_2$ on the basis of the discretized attributes.

(iv) New child nodes are generated with respect to the respective subsets. Further, the discretized attributes of the gas species Xmax are labeled to respective corresponding branches which connect a superordinate node (a parent node) with these new childe nodes (For example, in FIG. 7, "Gas 1" corresponds to "the superordinate node", "Gas 2", "Gas 3", and "Gas 4" correspond to "the child nodes" which correspond to the subsets, and "Large Amount", "Small Amount" and "Extremely Small Amount" correspond to the labels of the respective corresponding discretized attributes (branches)).

(v) When the number of pieces of abnormality case data in the generated child node is three or more, the subset of this childe node is further divided recursively in accordance with the processes (ii) to (iv). When the number of pieces of abnormality case data in a generated child node is less than three, this child node is defined as a leaf node, and the type of an internal abnormality that is the largest in number among internal abnormalities contained in the set of this leaf node is labeled to the leaf node as a solution. Further, when the number of pieces of abnormality case data is zero, the type of an internal abnormality that is the largest in number among internal abnormalities contained in the set of the superordinate node thereof is labeled to the leaf node as a solution. Further, when there are a plurality of types of internal abnormalities that are largest in number among internal abnormalities contained in the set of the leaf node, all of the types are labeled to the leaf node as solutions. In this case, the types may be labeled together with ratios of the types of internal abnormalities.

Here, a description will be made on the basis of an example shown in FIG. 12. Since six pieces of abnormality case data and four pieces of abnormality case data are respectively contained in "Superordinate Node" and "Child Node 1", each of a set of the "Superordinate Node" and a subset of the "Child Node 1" is recursively divided into subsets. Further, since two pieces of abnormality case data are contained in "Child Node 3", the "Child Node 3" is defined as a leaf node labeled as "Abnormality 1" which is the type of an internal abnormality that is the largest in number among internal abnormalities contained in the "Child Node 3". Further, since the number of pieces of the abnormality case data contained in "Child Node 2" is zero, the "Child Node 2" is defined as a leaf node labeled as "Abnormality 3" which is the type of an abnormality that is the largest in number among internal abnormalities contained in the "Superordinate Node".

(vi) After all of the above-described processes are finished, so-called pruning is performed. The pruning is performed when a relationship of "an error rate in a parent node"<"an error rate in its entire child nodes" is satisfied. After the pruning is performed, the parent node is defined as a leaf node, and the type of an internal abnormality that is the largest in number among internal abnormalities sorted in the child node is defined as a label of the leaf node.

As the error rate, a value that is calculated as a percent point obtained from upper cumulative probability of a beta distribution of 0.25 (a value of an inverse function of a cumulative distribution function of the beta distribution) with respect to the number of pieces of abnormality case data contained in the leaf node (defined as N) and the number of pieces of abnormality case data erroneously classified (defined as E) can be used. According to this, it is possible to estimate the error rate so as to be safer than the case where the error rate is calculated as the ratio between the above numbers (E/N).

Here, a description will be made on the basis of examples shown in FIGS. 13(a) and 13(b). When, as shown in FIG. 13(a), "Abnormality 3", "Abnormality 2" and "Abnormality 3" as three childe nodes are formed from "Gas 2" as a parent node at the stage of the process (v), if the error rate in the parent node is 11% and the error rate in the entire three child nodes is 16%, the child nodes are pruned as shown in FIG. 13(b). Further, the parent node which is labeled as "Gas 2" is temporality defined as a leaf node, and "Abnormality 3" which is the largest in number among internal abnormalities sorted in the previous child nodes is defined as a label of the leaf node.

(vii) The decision tree is completed when the above pruning is finished, and the thus generated decision tree is stored in the decision tree storage unit 11d. Further, the values calculated in the above processes may also be stored in the decision tree storage unit 11d.

Next, in step S205, the discretized data group of the determination target gases, the discretized data group being stored in the second discretized data group storage unit 11f, is applied to the decision tree stored in the decision tree storage unit 11d in the second internal abnormality determination unit 10e. Then, the type of the internal abnormality is determined as content of a finally found leaf node by following branches sequentially from a root node of the decision tree.

Here, a description will be made on the basis of an example shown in FIG. 7. Assuming that a part of the finally decided decision tree has a tree structure shown in FIG. 7, and the discretized data group of the determination target gases has characteristics such as "Gas 1: Large Amount, Gas 2:

Extremely Small Amount, Gas 3: Small Amount, Gas 4: Extremely Small Amount, Gas 5: Extremely Small Amount", "Gas 1" which is labeled to the root node of the decision tree is first selected from the discretized data group of the determination target gas, and a branch which is a discretized attribute thereof and labeled as "Large Amount" is selected. Then, "Gas 2" which is a subordinate node (a child node) of the root node is selected by following the selected branch, and a branch which is a discretized attribute thereof and labeled as "Extremely Small Amount" is selected. Further, "Gas 5" which is a further subordinate node is selected by following the selected branch, and a branch which is a discretized attribute thereof and labeled as "Extremely Small Amount" is selected to thereby finally reach "Abnormality 5" which is a leaf node. This "Abnormality 5" is a type of the internal abnormality of the determination target oil-filled electric device, the type being determined by the decision tree.

Further, in this case, a plurality of pieces of abnormality case data may be contained in the leaf node. For example, after the labeling, six pieces of abnormality case data and two pieces of abnormality case data are respectively contained in the Child Node 2 and the Child Node 3 both of which is a leaf node in FIG. 12. Further, in the Child Node 2, different types of internal abnormalities are contained. Further, as described above, as each of the types of internal abnormalities shown in the abnormality case data (the types of internal abnormalities shown in FIGS. 8 to 10, for example), a representative type among a plurality of types of internal abnormalities may be selected. In such a case, the type of the internal abnormality of the determination target apparatus can also be determined in such a manner that, with respect to all pieces of the abnormality case data contained in the leaf node, the ratio of the number of each type of the internal abnormalities to the total number of all types of the internal abnormalities contained in the abnormality case data is obtained as the probability of occurrence of each type of the internal abnormalities.

With the above processes, step S104 which is the diagnosis using the decision tree is finished, a result of the diagnosis of the internal abnormality performed in the second internal abnormality determination unit 10e is stored in the result storage unit (not shown) (step S105). Further, if necessary, the result of the diagnosis is output by the output means 3.

Although the present embodiment has been described as the abnormality diagnosis system for performing the abnormality diagnosis method of an oil-filled electric apparatus or the abnormality diagnosis method, a configuration with only the decision tree generation method which is performed in step S104 described above (steps S201 to S204) also falls within the scope of the present invention. Further, a program for causing a computer to execute respective steps of the abnormality diagnosis method or the decision tree generation method also falls within the scope of the present invention. This point is also the same as in the following embodiments.

Second Embodiment

Fuzzy Decision Tree

Next, the second embodiment of the present invention will be described. The present embodiment has the same configuration as the configuration of the first embodiment excepting that a decision tree that is generated on the basis of certainty factors (hereinafter, also referred to as a fuzzy decision tree) and a discretized data group of determination target gases both of which will be described later are used. Therefore, the same figures and the same reference numerals will be used to refer to the same parts as those described in the first embodiment, and a detailed description thereof will be omitted.

When a fuzzy decision tree is used, a discretized data group that is generated in step S203 shown in FIG. 4 is different from the discretized data group in the first embodiment.

That is, in the second embodiment, in the discretized data generation unit 10b, on the basis of the standardized data group of each of the abnormality cases, the data group being stored in the first standardized data group storage unit 11b, certainty factors corresponding to the respective concentration ratios of the respective gas species, the concentration ratios constituting the standardized data group, are calculated using predetermined membership functions which are set for the respective gas species. Further, a discretized data group is generated by converting the concentration ratios of the gas species into a plurality of discretized attributes on the basis of the certainty factors, and the thus generated discretized data group is stored in the first discretized data group storage unit 11c. Further, on the basis of the standardized data group of determination target gases, the data group being stored in the second standardized data group storage unit 11c, certainty factors corresponding to the respective concentration ratios of the respective gas species, the concentration ratios constituting the standardized data group, are calculated by predetermined membership functions which are set for the respective gas species. Further, a discretized data group is generated by converting the concentration ratios of the gas species into a plurality of discretized attributes on the basis of the certainty factors, and the thus generated discretized data group is stored in the second discretized data group storage unit 11f. The membership functions used for generating the discretized data group of each of the abnormality cases are the same as the membership functions used for generating the discretized data group of the determination target gases.

Each of the membership functions can be determined as follows when taking an example in which the number of the discretized attributes are three (that is, "Extremely Small Amount", "Small Amount" and "Large Amount").

Figure 14:
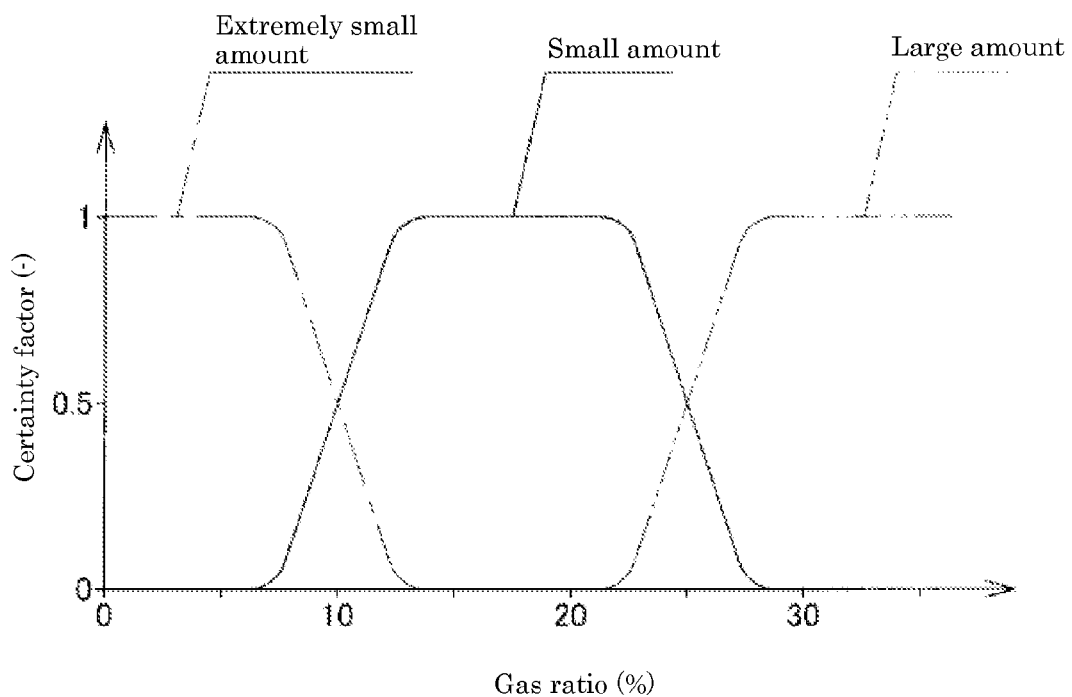
FIG. 14 is a schematic view illustrating a membership function of a certain gas species.

At first, a standardized data group of each of the gas species is extracted from the above-described first standardized data group which is obtained by converting the concentrations of the gas species into the ratios, and an average value and a maximum value of the concentration ratio of each of the gas species are calculated. The calculated average value of the concentration ratio is defined as a branch point between "Extremely Small Amount" and "Small Amount" (namely, a value in which the certainty factor of each of the discretized attributes becomes 0.5). Further, the calculated maximum value of the concentration ratio is defined as a branch point between "Small Amount" and "Large Amount" (namely, a value in which the certainty factor of each of the discretized attributes becomes 0.5). Then, on the basis of these branch points, a diagnostic specialist empirically obtains a relationship between the certainty factor of each of the discretized attributes and the gas concentration ratio from historical abnormality case data and the like to thereby generate a membership function. An example thereof is shown in FIG. 14.

Further, the sum of the certainty factors of the discretized attributes in the same gas ratio always becomes 1. Further, as described above, the membership function of each of the gas species is obtained on the basis of the value that is calculated from the first standardized data group which is based on the abnormality case data. Therefore, the membership function may be updated when a new abnormality case is added to the abnormality case data.

Here, the processing of the historical abnormality case data will be specifically described. For each of the cases, a discretized data group as shown in FIG. 15 is generated on the basis of, for example, a membership function as shown in FIG. 14 which is previously generated for each of the gas species. For example, in a case where the membership function shown in FIG. 14 has been generated with respect to "Gas 1" which is a gas species in FIG. 15, when the gas ratio in the standardized data which has been generated in step S202 is 9%, the certainty factors of the discretized attributes of "Small Amount" and "Extremely Small Amount" respectively become 0.30 and 0.70, from the graph (the membership function) shown in FIG. 14. That is, in the case of FIG. 15, the number of the discretized attribute of "Small Amount" is counted as 0.30 and the number of the discretized attribute of "Extremely Small Amount" is counted as 0.70 with respect to "Gas 1".

After the discretized data group is generated in this manner in step S203, a decision tree (a fuzzy decision tree) is generated and stored in the decision tree storage unit 11*d* in the same manner as in the first embodiment (step S204). Further, the above-described formulae (5) to (8) which are used for generation of the fuzzy decision tree differ from the formulae (1) to (4) in the first embodiment in that some of the parameters used in the formulae of the second embodiment are certainty factors. However, the processing method is the same as in the first embodiment, a detailed description thereof will therefore be omitted.

In determination of the type of the internal abnormality using the decision tree (fuzzy decision tree) in step S205, a substantive procedure is the same as the procedure in the first embodiment. A difference therebetween is that, in the second embodiment, there is a case of reaching a plurality of leaf nodes by following a plurality of branches because the second discretized data group is sorted into discretized attributes on the basis of the certainty factors. In this case, among the sums of the certainty factors of the respective plurality of types of internal abnormalities of the fuzzy decision tree, the internal abnormalities being contained in these leaf nodes, the type of an internal abnormality having the largest value is the type of the internal abnormality of the determination target oil-filled electric apparatus which is determined by the fuzzy decision tree. Further, in the same manner as in the first embodiment, the type of the internal abnormality of the determination target apparatus may be determined as the probability of occurrence of each type of internal abnormalities.

Third Embodiment

Abnormality Predictive Diagnosis Method

Next, the third embodiment of the present invention will be described.

Figure 2:
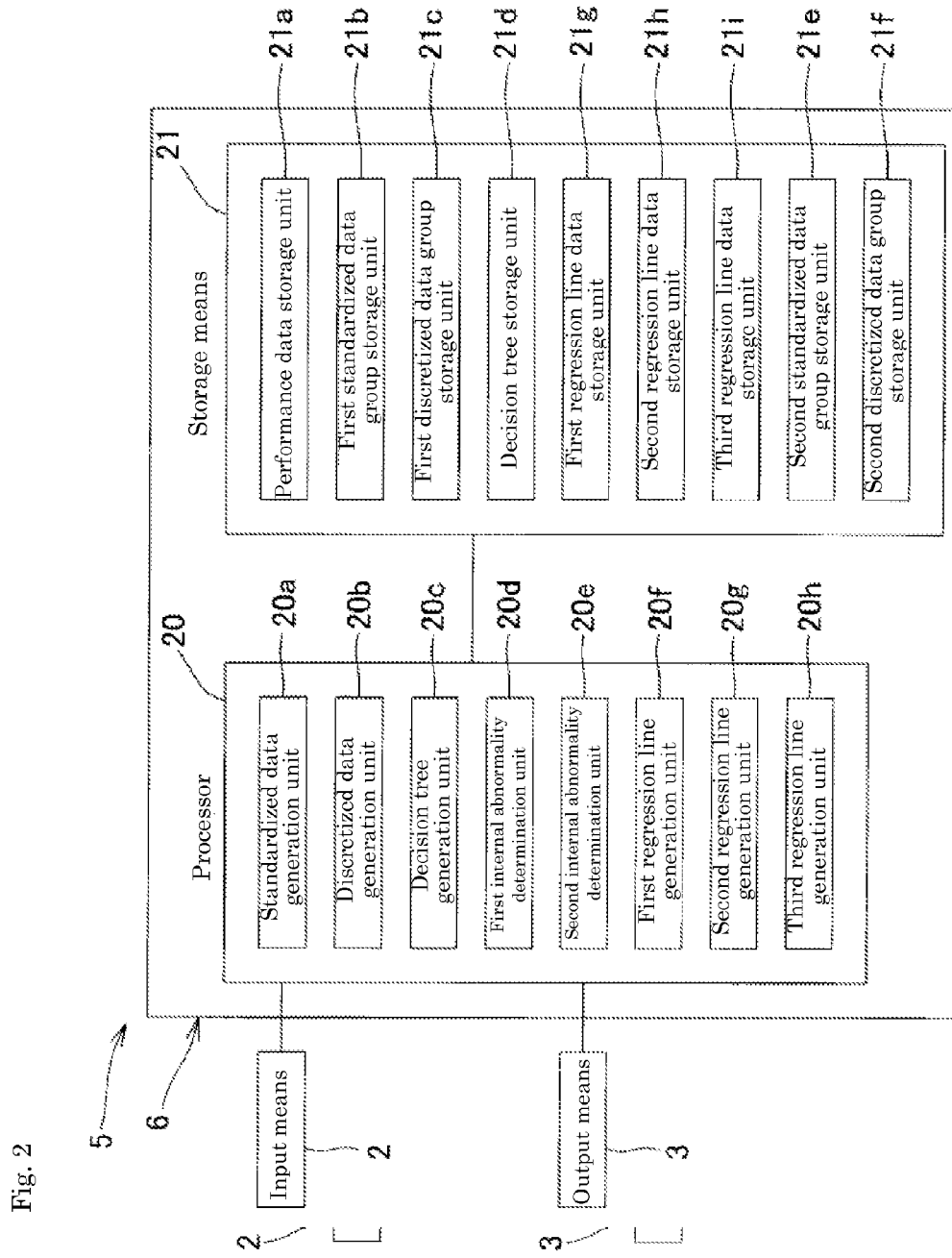
FIG. 2 is a block diagram illustrating a main configuration of a representative abnormality predictive diagnosis system for performing an abnormality predictive diagnosis method of an oil-filled electric apparatus according to the present invention.

FIG. 2 is a block diagram illustrating a main configuration of a representative abnormality predictive diagnosis system for performing an abnormality predictive diagnosis method of an oil-filled electric apparatus according to the present invention in which a configuration for predicting the concentrations of the determination target gas species is added to the system configuration shown in FIG. 1. Therefore, the configurations of the units 20*a* to 20*e* and 21*a* to 21*f* in FIG. 2 are respectively the same as the configurations of the units 10*a* to 10*e* and 11*a* to 11*f* in FIG. 1.

Figure 5:
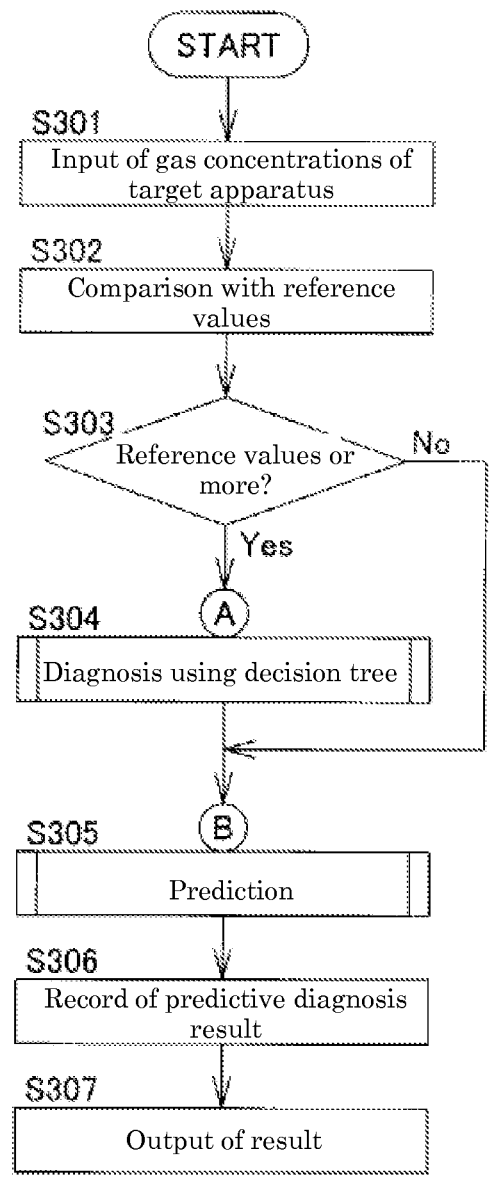
FIG. 5 is a schematic flow chart illustrating a flow from input of concentrations of determination target gases until obtaining a result of abnormality predictive diagnosis.

Further, FIG. 5 is a schematic flow chart illustrating a flow from input of the concentrations of the determination target gases until obtaining a result of the abnormality predictive diagnosis. As shown in FIG. 5, the present embodiment is completely the same as the first embodiment excepting that a prediction step of step S305 is performed. Therefore, steps S301 to S304, S306, and S307 in FIG. 5 are respectively the same as steps S101 to S106 in FIG. 3.

As described above, the third embodiment has the same configuration as the configuration of the first embodiment excepting that the system of the third embodiment includes the configuration for performing prediction. Therefore, a detailed description of the configuration in common will be omitted.

In the third embodiment, as shown in FIG. 2, a first regression line generation unit 20*f*, a second regression line generation unit 20*g*, and a third regression line generation unit 20*h* are provided in a processor 20 in addition to the configuration of the processor 10 in FIG. 1. Further, a first regression line data storage unit 21*g*, a second regression line data storage unit 21*h*, and a third regression line data storage unit 21*i* are provided in storage means 21 in addition to the configuration of the storage means 11 in FIG. 1.

The first regression line generation unit 20*f* has a function to calculate, with respect to a time series data group of gas concentration, the data group being extracted for each of a plurality of gas species dissolved in an insulation oil in a determination target oil-filled electric apparatus on the basis of three or more pieces of historical performance data of the determination target oil-filled electric apparatus, the performance data being stored in the performance data storage unit 20*a*, a first regression line, dispersion of the time series data group with respect to the first regression line, and uncertainty that is based on the dispersion, and store the time series data group, the first regression line, the dispersion and the uncertainty in the first regression line data storage unit 21*g*.

The second regression line generation unit 20*g* has a function to calculate, with respect to the latest three or more pieces of the performance data in the above-described time series data group which is extracted on the basis of the performance data stored in the performance data storage unit 21*a*, a second regression line and a first predicted gas concentration which is a gas concentration at the time when a predetermined period of time has passed from the latest measurement time on the second regression line, and store the second regression line and the first predicted gas concentration in the second regression line data storage unit 21*h*.

The third regression line generation unit 20*h* has a function to calculate the sum of the uncertainty which is stored in the first regression line data storage unit 21*g* and the first predicted gas concentration which is stored in the second regression line data storage unit 21*h* as a second predicted gas concentration, generate a predicted time series data group which is composed of the second predicted gas concentration and the latest piece of the performance data in the time series data group which is extracted on the basis of the performance data stored in the performance data storage unit 21*a*, generate a third regression line with respect to the predicted time series data group, and store the third regression line in the third regression line data storage unit 21*i*.

Next, among the processing procedures in the abnormality predictive diagnosis system according to the present invention, a processing procedure for performing prediction will be described on the basis of an embodiment.

As shown in FIG. 5, in the present embodiment, not only when the concentrations of the determination target gases are less than the respective reference values, but also when the concentrations of the determination gases are equal to or more than the respective reference values in step S303, prediction of the determination target gas concentrations is performed in step S305. By performing the prediction also when the concentrations of the determination target gases are equal to or more than the respective reference values, it is possible to appropriately figure out the time for repair and replacement of the oil-filled electric apparatus as a determination target. However, when the gas concentrations are equal to or more than the respective reference values, the prediction may not be performed.

Figure 6:
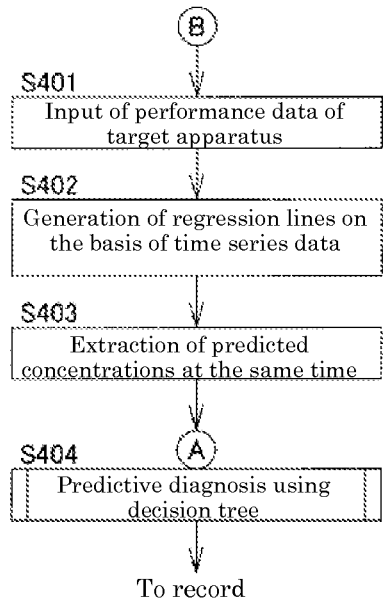
FIG. 6 is a schematic flow chart illustrating details of a step of prediction in FIG. 5 (step S305).
Figure 16:
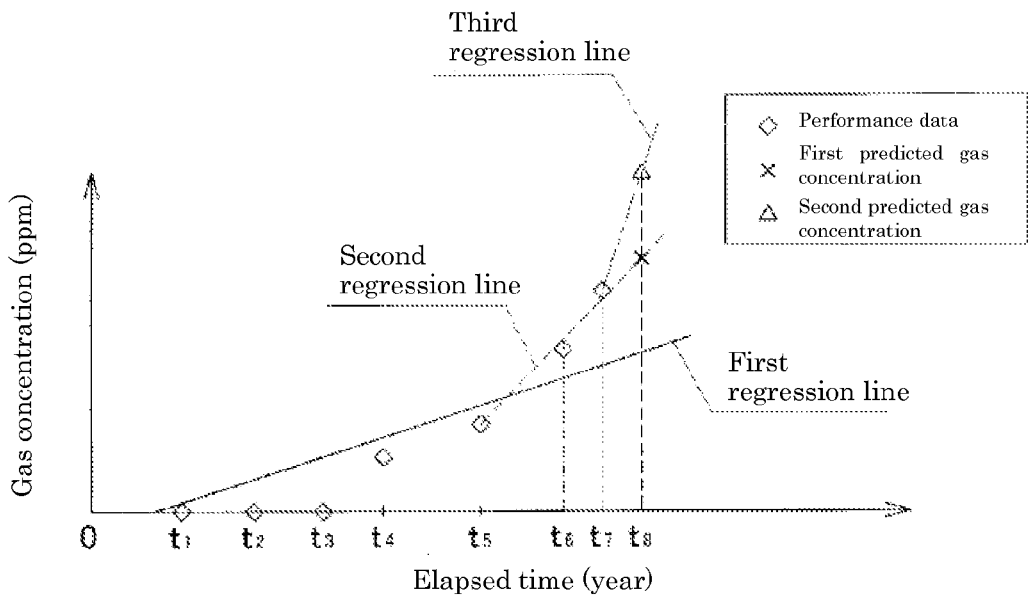
FIG. 16 is a schematic view illustrating a procedure for generating regression lines which are based on a time series data group of a gas concentration of a certain gas species.

FIG. 6 is a schematic flow chart illustrating details of a step of prediction in FIG. 5 (step S305). Further, FIG. 16 is a schematic view illustrating a procedure for generating regression lines which are based on a time series data group of the gas concentration of a certain gas species. Further, in FIG. 16, a zero point of the horizontal axis representing elapsed time indicates a time at which an oil-filled electric apparatus is newly installed. Therefore, when the oil-filled electric apparatus is repaired, the repaired time becomes the newly installed time, namely, the zero point. Accordingly, time series data before the zero point will not be referenced in the prediction step.

In step S305, three or more pieces of historical performance data of the determination target oil-filled electric apparatus, the performance data being stored in the performance data storage unit 20a, are first selected in the first regression line generation unit 20f (step S401).

Then, a first regression line is calculated with respect to a time series data group of the gas concentration, the data group being extracted for each of a plurality of gas species dissolved in the insulating oil in the oil-filled electric apparatus on the basis of the selected pieces of the performance data. The first regression line can be calculated by a least squares method.

Further, dispersion of the time series data group with respect to the first regression line and uncertainty that is based on the dispersion are calculated. Then, these calculated results together with the time series data group are stored in the first regression line data storage unit 21g.

The dispersion is a difference between a concentration $a_p$ of a certain gas species at a certain time $t_p$ in the time series data group and a calculated concentration $a_p'$ of this gas species at the time $t_p$, the concentration $a_p'$ being calculated by the first regression line. For example, when the first regression line is expressed by "$a=\alpha t+\beta$ (a: the concentration of a certain gas species, t: elapsed time, $\alpha$ and $\beta$: arbitrary constants)", a dispersion $D_p$ at a certain time $t_p$ is "$D_p=a_p'-a_p=\alpha t_p+\beta-a_p$".

Further, the uncertainty (U) is expressed by the following formula (9) in a case where the above-described dispersion is calculated with respect to all pieces of data in the time series data group, and each dispersion is defined as $D_p$ (p=natural numbers 1 to P, P: a value that is equal to the number of all pieces of data contained in time series data of a certain gas species). Further, the uncertainty is preferably calculated with a 95% of confidence level.

[Mathematical 28]

$$U = \sqrt{\frac{\sum_{p=1}^{P} D_p^2}{P}} \times 1.96 \qquad \text{Formula (9)}$$

Further, in the second regression line generation unit 20g, a second regression line is calculated with respect to the latest three or more pieces of the performance data in the above-described time series data group which is extracted on the basis of the performance data stored in performance data storage means (in this embodiment, the time series data group stored in the first regression line data storage unit 21g). Further, a first predicted gas concentration which is a gas concentration at the time when a predetermined period of time has passed from the latest measurement time on the second regression line is calculated. Then, the second regression line and the first predicted gas concentration are stored in the second regression line data storage unit 21h.

The above-described predetermined period of time indicates, in principle, a period of time that is the same as a period of time between the latest measurement time and the second latest measurement time. However, the predetermined period of time is not necessarily such a period of time, but may be determined on the basis of time of measurement that is planned to be performed in the future.

Since the second regression line is separately generated on the basis of the latest three or more pieces of the performance data in this manner, it is possible to reflect the most recent data transition.

Here, a description will be made on the basis of FIG. 16. In the time series data group, the second regression line is calculated with respect to pieces of the performance data at the latest three measurement times including $t_7$ (the latest measurement time), $t_6$ (the second latest measurement time) and $t_5$. Then, the first predicted gas concentration on the second regression line at a predetermined time $t_8$ is calculated (represented as "×" in FIG. 16). The predetermined time $t_8$ is defined by "$t_8-t_7=t_7-t_6$".

Further, in the third regression line generation unit 20h, the sum of the uncertainty which is stored in the first regression line data storage unit 21g and the first predicted gas concentration which is stored in the second regression line data storage unit 21h is calculated as a second predicted gas concentration. Further, a predicted time series data group which is composed of the second predicted gas concentration and the latest piece of the performance data in the time series data group which is extracted on the basis of the performance data stored in the performance data storage unit 21a (in this embodiment, the time series data group stored in the first regression line data storage unit 21g) is generated. Further, a third regression line is generated with respect to the predicted time series data group, and then stored in the third regression line data storage unit 21i.

Calculating the second predicted gas concentration by adding the uncertainty which is obtained on the basis of all pieces of the data in the time series data group to the first predicted gas concentration on the second regression line which is generated from the latest three or more pieces of the data in the time series data group in this manner makes it possible to estimate the second predicted gas concentration to the safe side by taking into consideration the dispersion in the entire time series data group.

Here, a description will be made on the basis of FIG. 16. A second predicted gas concentration c ($t_8$) (the gas concentration "Δ" in FIG. 16) is calculated by adding the above-described specific uncertainty to a first predicted gas concentration b ($t_8$) which is a gas concentration at a time $t_8$ on the second regression line (the gas concentration "×" in FIG. 16). Further, a predicted time series data group is generated from the second predicted gas concentration c ($t_8$) at the time $t_8$ and a gas concentration a ($t_7$) at a time $t_7$ which is the latest piece of the performance data in the above-described time series data group. After that, a third regression line is generated on the basis of the thus generated predicted time series data group.

As described above, the regression lines are generated with respect to each of the determination target gas species in step S402.

Next, after the generation of the third regression line is performed, third predicted gas concentrations at the same time on the respective third regression lines are extracted for the respective gas species (step S403). The time at which the third predicted gas concentrations of the respective gas species are extracted is not limited to any specific time as long as it is the same time among all of the gas species. However, in view of the fact that abnormality diagnosis is performed by predictive diagnosis using a decision tree which is a later process (step S404), the time is preferably one at which any of the third predicted gas concentrations become equal to or larger than the respective predetermined reference values as a determination criterion in step S302. Further, the calculated third predicted gas concentrations may be stored in the third regression line data storage unit 21i. Further, the third predicted gas concentrations may be output by the output means 3.

Next, predictive diagnosis using a decision tree is performed by using the third predicted gas concentrations (step S404).

The process performed in step S404 is substantially the same as the diagnosis using the decision tree which is performed in the first embodiment excepting that the third predicted gas concentrations are used instead of the concentrations of the determination target gases in steps S201 to S205. Therefore, a detailed description thereof will be omitted. However, in the third embodiment, it is preferred that a storage unit for a data group which is based on the performance data of the concentrations of the determination target gases and a storage unit for a data group which is based on the third predicted gas concentrations (both of which are not shown) be respectively provided in the second standardized data group storage unit 21e and the second discretized data group storage unit 21f.

Further, in the third embodiment, the fuzzy decision tree of the second embodiment may be employed instead of the decision tree of the first embodiment.

EXAMPLE

Hereinbelow, examples of the above-described embodiments will be shown.

Example 1

In an example 1, five types of internal abnormalities including abnormality in a tap portion, abnormality in an iron core portion, abnormality in a coil portion, abnormality in a lead portion, and oil leakage from a switch cell were used as the type of the internal abnormality. Further, ten types of gas species including methane, ethane, ethylene, propane, propylene, isobutane, acetylene, hydrogen, carbon monoxide, and normal butane were used as the gas species. Further, three discretized attributes including "Large Amount", "Small Amount" and "Extremely Small Amount" were determined on the basis of thresholds which are based on determination by a diagnostic specialist. Then, with respect to a transformer as an oil-filled electric apparatus, the decision tree of the first embodiment (which is shown as "Normal" in Table 1) was generated on the basis of 444 pieces of historical abnormality case data. In addition, each of the 444 pieces of abnormality case data as a determination target was applied to the generated decision tree to thereby determine the type of the internal abnormality of the determination target apparatus. The accuracy rates in the respective types of internal abnormalities and in total based on a result of the determination using the decision tree (the type of an internal abnormality which is labeled to a finally found leaf node) are shown in Table 1.

As shown in Table 1, all of the accuracy rates in the respective types of internal abnormalities were 60% or more, and the accuracy rate in total was 76.4%. The accuracy rate of an average diagnostic specialist is generally about 50%, and the accuracy rate of a skilled diagnostic specialist is generally about 80%. Therefore, the diagnosis method in the present embodiment has a diagnostic accuracy that is higher than the diagnostic accuracy of an average diagnostic specialist, and is very close to the diagnostic accuracy of a skilled diagnostic specialist.

Embodiment 2

The type of the internal abnormality of the determination target apparatus was determined in the same manner as in the example 1 excepting that the decision tree of the second embodiment (which is shown as "Fuzzy" in Table 1) was generated, and each of the 444 pieces of abnormality case data sets as a determination target was applied to the generated fuzzy decision tree. The accuracy rates in the respective types of internal abnormalities and in total based on a result of the determination using the fuzzy decision tree are shown in Table 1.

As shown in Table 1, all of the accuracy rates in the respective types of internal abnormalities were 62% or more, and the accuracy rate in total was 80.4%. By using the fuzzy decision tree, the diagnostic accuracy is further improved. The accuracy rate in total is equal to the diagnostic accuracy of a skilled diagnostic specialist.

TABLE 1

| | | Example 1 | Examp 2 |
|---|---|---|---|
| Decision Tree | | Normal | Fuzzy |
| Accuracy | Tap Portion | 84.7 | 91.3 |
| Rate of | Iron Core | 72.6 | 80.0 |
| Internal | Portion | | |
| Abnormality | Coil Portion | 76.0 | 74.7 |
| (%) | Lead Portion | 64.8 | 62.0 |
| | Oil Leakage | 60.0 | 70.0 |
| | Total | 76.4 | 80.4 |

Example 3

Figure 17:
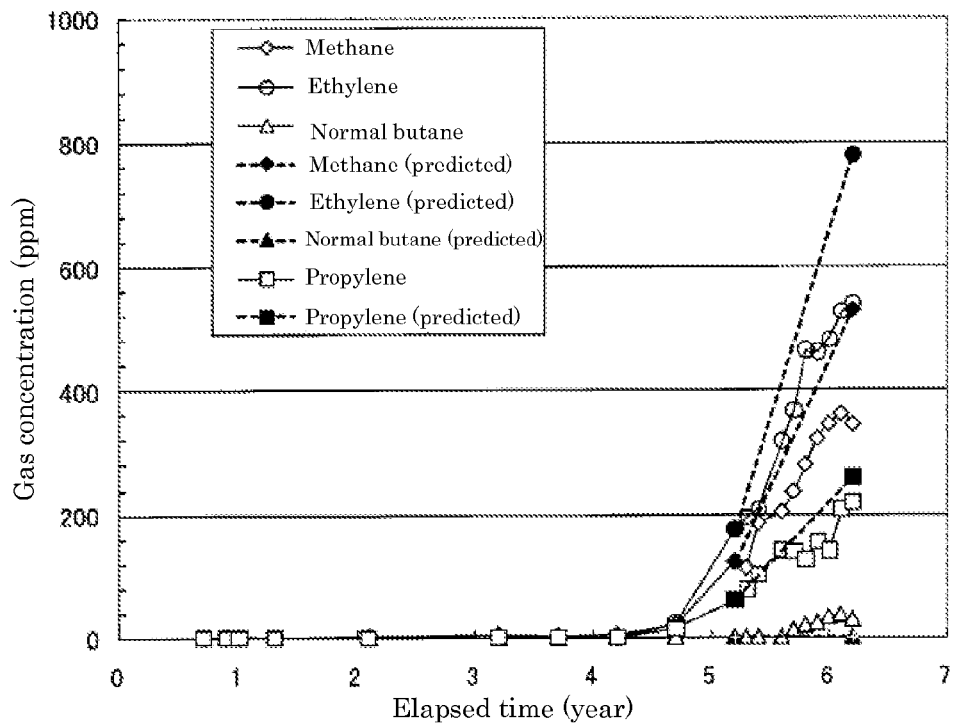
FIG. 17 is a diagram graphically illustrating time series data groups and third regression lines of respective gas species in a third embodiment.
Figure 18:
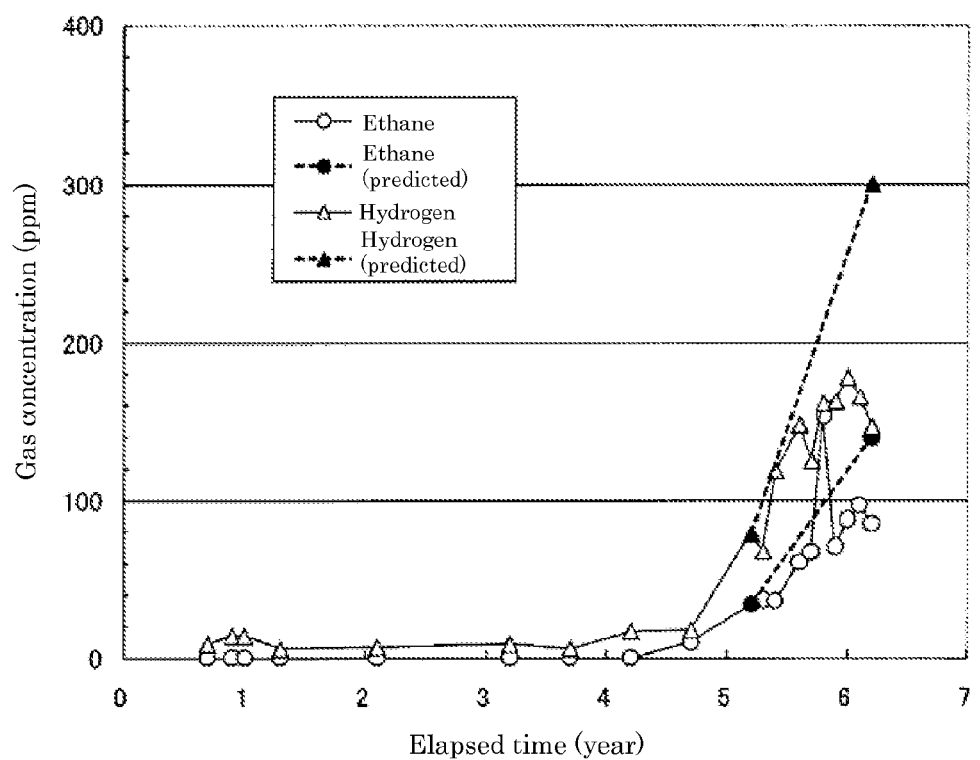
FIG. 18 is a diagram graphically illustrating time series data groups and third regression lines of respective gas species in the third embodiment.
Figure 19:
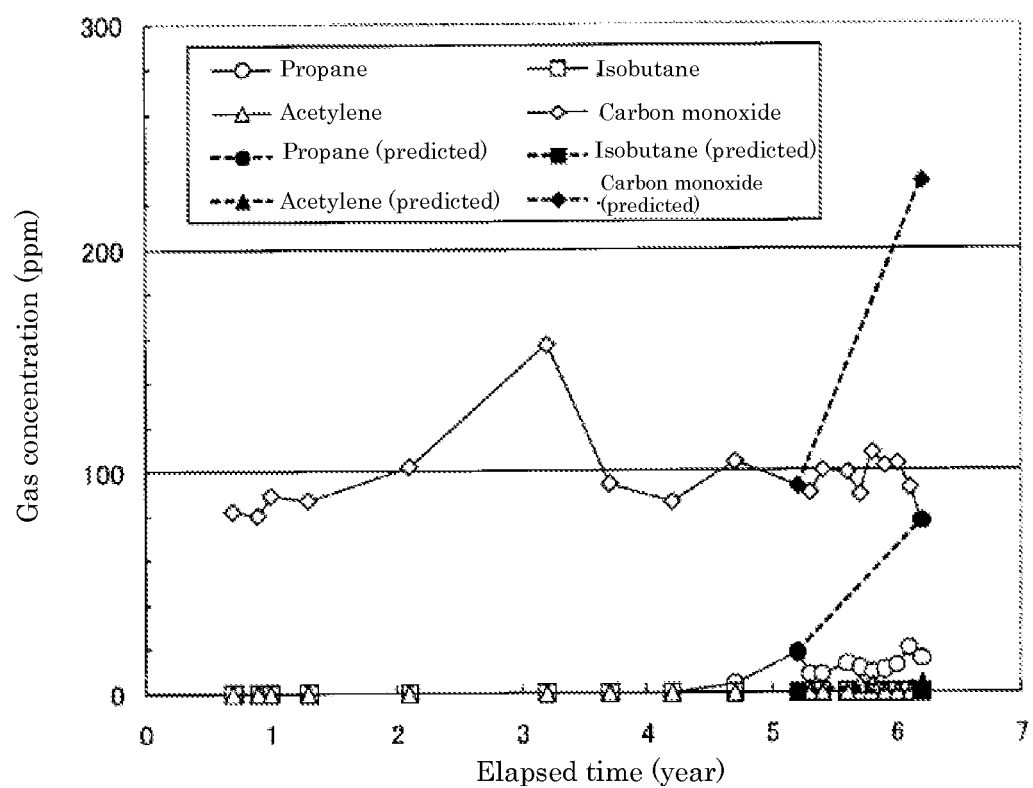
FIG. 19 is a diagram graphically illustrating time series data groups and third regression lines of respective gas species in the third embodiment.

The decision tree of the first embodiment was generated in the same manner as in the example 1. Further, on the basis of time series data group of about past five years in a time series data group of past six years of a specific transformer which actually had an internal abnormality in an iron core portion (measured data from 0 to 5.2 years in FIGS. 17 to 19), third predicted gas concentrations of the respective gas species were calculated according to the above-described third embodiment. The calculated results are shown in Table 2. As shown in FIGS. 17 to 19, the time series data group is composed of three or more pieces of time series data for the respective gas species at the time when 5.2 years have passed. Each of the third predicted gas concentration is a predicted concentration ("Predicted Value" of "Gas Concentration after 6 Years" in Table 2) at the time when one year has passed since the latest measurement time (namely, when the elapsed time becomes 5.2 years in FIGS. 17 to 19. The values thereof are shown in "Gas Concentration after 5 Years" in Table 2).

A predetermined process was performed on the third predicted gas concentrations, and the decision tree was applied thereto to thereby make predictive diagnosis on the type of an internal abnormality of the transformer, the internal abnormality being predicted to occur after one year. Further, the internal abnormality diagnosis was performed also on the gas concentrations after 5 years and 6 years. The diagnosis results are shown in Table 2. In Table 2, "ND" indicates that no internal abnormality was detected.

As shown in FIGS. 17 to 19, each of the third regression lines (broken lines in FIGS. 17 to 19) and the measured value exhibit generally the same tendency. Further, the predicted values are generally larger than the respective measured values. Therefore, an excellent result was obtained from a standpoint of safety of the prediction. Further, as shown in Table 2, all of the results of the internal abnormality diagnoses using the decision tree indicate that the internal abnormality occurred in the iron core portion, which agreed with the type of the internal abnormality which has actually occurred.

TABLE 2

|  | Gas Concentration after 5 Years (ppm) | Gas Concentration after 6 Years | |
| --- | --- | --- | --- |
|  |  | Predicted Value (ppm) | Measured Value (ppm) |
| Methane | 123 | 530 | 346 |
| Ethane | 34 | 140 | 85 |
| Ethylene | 176 | 780 | 540 |
| Propane | 18 | 77 | 15 |
| Propylene | 61 | 260 | 218 |
| Isobutane | ND | ND | ND |
| Acetylene | 1 | 4 | 1 |
| Hydrogen | 79 | 300 | 147 |
| Carbon Monoxide | 93 | 230 | 77 |
| Normal Butane | ND | ND | 29 |
| Internal Abnormality | Iron Core Portion | Iron Core Portion | Iron Core Portion |

REFERENCE SIGNS LIST 1 diagnosis system
2 input means
3 output means
4, 6 computer
5 predictive diagnosis system
10 processor
10a standardized data generation unit
10b discretized data generation unit
10c decision tree generation unit
10d first internal abnormality determination unit
10e second internal abnormality determination unit
11 storage means
11a performance data storage unit
11b first standardized data group storage unit
11c first discretized data group storage unit
11d decision tree storage unit
11e second standardized data group storage unit
11f second discretized data group storage unit
20 processor
20a standardized data generation unit
20b discretized data generation unit
20c decision tree generation unit
20d first internal abnormality determination unit
20e second internal abnormality determination unit
20f first regression line generation unit
20g second regression line generation unit
20h third regression line generation unit
21 storage means
21a performance data storage unit
21b first standardized data group storage unit
21c first discretized data group storage unit
21d decision tree storage unit
21e second standardized data group storage unit
21f second discretized data group storage unit
21g first regression line data storage unit
21h second regression line data storage unit
21i third regression line data storage unit

The invention claimed is:

1. An abnormality diagnosis method of an oil-filled electric apparatus in which an internal abnormality of an oil-filled electric apparatus is diagnosed using a computer, the method comprising the steps, by a computer, of:

generating, on the basis of historical abnormality case data of an oil-filled electric apparatus, the historical abnormality case data being stored in performance data storage means, a standardized data group by converting concentrations of a plurality of gas species dissolved in an insulating oil in the oil-filled electric apparatus into ratios for each of abnormality cases, and storing the standardized data group in first standardized data group storage means;

generating, on the basis of the standardized data group of each of the abnormality cases, the standardized data group being stored in the first standardized data group storage means, a discretized data group by converting the ratios of the concentrations of the gas species, the ratios constituting the standardized data group, into a plurality of discretized attributes using predetermined thresholds set for the respective gas species, and storing the discretized data group in first discretized data group storage means;

generating a decision tree for determining a type of an internal abnormality of an oil-filled electric apparatus by analysis using the following formulae (1) to (4) on the basis of the discretized data group of each of the abnormality cases, the discretized data group being stored in the first discretized data group storage means, and storing the decision tree in decision tree storage means;

generating a standardized data group by converting concentrations of a plurality of gas species dissolved in an insulating oil taken from a determination target oil-filled electric apparatus into ratios, and storing the standardized data group in second standardized data group storage means;

generating, on the basis of the standardized data group of the determination target apparatus, the standardized data group being stored in the second standardized data group storage means, a discretized data group by converting the ratios of the concentrations of the gas species, the ratios constituting the standardized data group, into a plurality of discretized attributes using the same predetermined thresholds as in the abnormality cases, the predetermined thresholds being set for the respective gas species, and storing the discretized data group in second discretized data group storage means; and determining a type of an internal abnormality of the determination target apparatus by using the discretized data group of the determination target apparatus, the discretized data group being stored in the second discretized data group storage means, and the decision tree stored in the decision tree storage means;

[Mathematical 1]

$$G(X) = \frac{M(D) - E(X)}{S(X)} \quad \text{Formula (1)}$$

[Mathematical 2]

$$M(D) = \sum_{i=l}^{n} \left[ -\frac{C_i}{|D|} \log_2 \frac{C_i}{|D|} \right] \quad \text{Formula (2)}$$

[Mathematical 3]

$$E(X) = \sum_{j=l}^{v} \left[ \frac{\alpha_j}{|D|} \sum_{k=l}^{m} \left[ -\frac{\beta_{jk}}{\alpha_j} \log_2 \frac{\beta_{jk}}{\alpha_j} \right] \right] \quad \text{Formula (3)}$$

[Mathematical 4]

$$S(X) = \sum_{j=l}^{v} \left[ -\frac{\alpha_j}{|D|} \log_2 \frac{\alpha_j}{|D|} \right] \quad \text{Formula (4)}$$

X: a gas species dissolved in an insulating oil
D: a set of abnormality case data mapped to a node
|D|: the number of pieces of abnormality case data mapped to a node
$C_i$: the number of the i-th type of internal abnormalities in a set D
$\alpha_j$: the number of pieces of abnormality case data at the j-th branch of a gas species X
$\beta_{jk}$: the number of the k-th type of internal abnormalities at the j-th branch of a gas species X
G (X): a gain ratio
M (D): the amount of expected information with respect to the type of the internal abnormality in a set D
E (X): the amount of expected information after classification by a gas species X
S (X): the amount of expected information with respect to a gas species X in a set D
l: the type or a number of a discretized attribute of the first internal abnormality in a set D
m, n: the total number of types of internal abnormalities in a set D
v: the total number of discretized attributes.

2. The abnormality diagnosis method of an oil-filled electric apparatus according to claim 1, wherein the computer determines as to whether or not the gas concentrations of the plurality of gas species dissolved in the insulating oil taken from the determination target oil-filled electric apparatus fall within respective predetermined normal ranges, and performs abnormality determination using the decision tree only when there is an abnormal gas species.

3. An abnormality diagnosis system of an oil-filled electric apparatus comprising a computer, the computer diagnosing an internal abnormality of an oil-filled electric apparatus, the computer including:
performance data storage means for storing historical abnormality case data of an oil-filled electric apparatus;
first standardized data group generation means for generating, on the basis of historical abnormality case data of the oil-filled electric apparatus, the historical abnormality case data being stored in the performance data storage means, a standardized data group by converting concentrations of a plurality of gas species dissolved in an insulating oil in the oil-filled electric apparatus into ratios for each of abnormality cases;
first standardized data group storage means for storing the standardized data group generated by the first standardized data group generation means;
first discretized data group generation means for generating, on the basis of the standardized data group of each of the abnormality cases, the standardized data group being stored in the first standardized data group storage means, a discretized data group by converting the ratios of the concentrations of the gas species, the ratios constituting the standardized data group, into a plurality of discretized attributes using predetermined thresholds set for the respective gas species;
first discretized data group storage means for storing the discretized data group generated by the first discretized data group generation means;
decision tree generation means for generating a decision tree for determining a type of an internal abnormality of an oil-filled electric apparatus by analysis using the following formulae (1) to (4) on the basis of the discretized data group of each of the abnormality cases, the discretized data group being stored in the first discretized data group storage means;
decision tree storage means for storing the decision tree generated by the decision tree generation means;
second standardized data group generation means for generating a standardized data group by converting concentrations of a plurality of gas species dissolved in an insulating oil taken from a determination target oil-filled electric apparatus into ratios;
second standardized data group storage means for storing the standardized data group generated by the second standardized data group generation means;
second discretized data group generation means for generating, on the basis of the standardized data group of the determination target apparatus, the standardized data group being stored in the second standardized data group storage means, a discretized data group by converting the ratios of the concentrations of the gas species, the ratios constituting the standardized data group, into a plurality of discretized attributes using the same predetermined thresholds as in the abnormality cases, the predetermined thresholds being set for the respective gas species;
second discretized data group storage means for storing the discretized data group generated by the second discretized data group generation means; and
abnormality determination means for determining a type of an internal abnormality of the determination target apparatus by using the discretized data group of the determination target apparatus, the discretized data group being stored in the second discretized data group storage means, and the decision tree stored in the decision tree storage means;

[Mathematical 5]

$$G(X) = \frac{M(D) - E(X)}{S(X)} \quad \text{Formula (1)}$$

[Mathematical 6]

$$M(D) = \sum_{i=l}^{n} \left[ -\frac{C_i}{|D|} \log_2 \frac{C_i}{|D|} \right] \quad \text{Formula (2)}$$

[Mathematical 7]

$$E(X) = \sum_{j=l}^{v} \left[ \frac{\alpha_j}{|D|} \sum_{k=l}^{m} \left[ -\frac{\beta_{jk}}{\alpha_j} \log_2 \frac{\beta_{jk}}{\alpha_j} \right] \right] \quad \text{Formula (3)}$$

[Mathematical 8]

$$S(X) = \sum_{j=l}^{v} \left[ -\frac{\alpha_j}{|D|} \log_2 \frac{\alpha_j}{|D|} \right] \quad \text{Formula (4)}$$

X: a gas species dissolved in an insulating oil
D: a set of abnormality case data mapped to a node
|D|: the number of pieces of abnormality case data mapped to a node
$C_i$: the number of the i-th type of internal abnormalities in a set D
$\alpha_j$: the number of pieces of abnormality case data at the j-th branch of a gas species X
$\beta_{jk}$: the number of the k-th type of internal abnormalities at the j-th branch of a gas species X
G (X): a gain ratio
M (D): the amount of expected information with respect to the type of the internal abnormality in a set D
E (X): the amount of expected information after classification by a gas species X
S (X): the amount of expected information with respect to a gas species X in a set D
l: the type or a number of a discretized attribute of the first internal abnormality in a set D
m, n: the total number of types of internal abnormalities in a set D
v: the total number of discretized attributes.

4. An abnormality diagnosis program of an oil-filled electric apparatus in which an internal abnormality of an oil-filled electric apparatus is diagnosed using a computer, the program, stored on a non-transitory computer medium, causing the computer to execute the steps of:
generating, on the basis of historical abnormality case data of an oil-filled electric apparatus, the historical abnormality case data being stored in performance data storage means, a standardized data group by converting concentrations of a plurality of gas species dissolved in an insulating oil in the oil-filled electric apparatus into ratios for each of abnormality cases, and storing the standardized data group in first standardized data group storage means;
generating, on the basis of the standardized data group of each of the abnormality cases, the standardized data group being stored in the first standardized data group storage means, a discretized data group by converting the ratios of the concentrations of the gas species, the ratios constituting the standardized data group, into a plurality of discretized attributes using predetermined thresholds set for the respective gas species, and storing the discretized data group in first discretized data group storage means;
generating a decision tree for determining a type of an internal abnormality of an oil-filled electric apparatus by analysis using the following formulae (1) to (4) on the basis of the discretized data group of each of the abnormality cases, the discretized data group being stored in the first discretized data group storage means, and storing the decision tree in decision tree storage means;
generating a standardized data group by converting concentrations of a plurality of gas species dissolved in an insulating oil taken from a determination target oil-filled electric apparatus into ratios, and storing the standardized data group in second standardized data group storage means;
generating, on the basis of the standardized data group of the determination target apparatus, the standardized data group being stored in the second standardized data group storage means, a discretized data group by converting the ratios of the concentrations of the gas species, the ratios constituting the standardized data group, into a plurality of discretized attributes using the same predetermined thresholds as in the abnormality cases, the predetermined thresholds being set for the respective gas species, and storing the discretized data group in second discretized data group storage means; and
determining a type of an internal abnormality of the determination target apparatus by using the discretized data group of the determination target apparatus, the discretized data group being stored in the second discretized data group storage means, and the decision tree stored in the decision tree storage means;

[Mathematical 9]
$$G(X) = \frac{M(D) - E(X)}{S(X)} \qquad \text{Formula (1)}$$

[Mathematical 10]
$$M(D) = \sum_{i=l}^{n} \left[ -\frac{C_i}{|D|} \log_2 \frac{C_i}{|D|} \right] \qquad \text{Formula (2)}$$

[Mathematical 11]
$$E(X) = \sum_{j=l}^{v} \left[ \frac{\alpha_j}{|D|} \sum_{k=l}^{m} \left[ -\frac{\beta_{jk}}{\alpha_j} \log_2 \frac{\beta_{jk}}{\alpha_j} \right] \right] \qquad \text{Formula (3)}$$

[Mathematical 12]
$$S(X) = \sum_{j=l}^{v} \left[ -\frac{\alpha_j}{|D|} \log_2 \frac{\alpha_j}{|D|} \right] \qquad \text{Formula (4)}$$

X: a gas species dissolved in an insulating oil
D: a set of abnormality case data mapped to a node
|D|: the number of pieces of abnormality case data mapped to a node
$C_i$: the number of the i-th type of internal abnormalities in a set D
$\alpha_j$: the number of pieces of abnormality case data at the j-th branch of a gas species X
$\beta_{jk}$: the number of the k-th type of internal abnormalities at the j-th branch of a gas species X
G (X): a gain ratio
M (D): the amount of expected information with respect to the type of the internal abnormality in a set D
E (X): the amount of expected information after classification by a gas species X
S (X): the amount of expected information with respect to a gas species X in a set D
l: the type or a number of a discretized attribute of the first internal abnormality in the set D
m, n: the total number of types of internal abnormalities in a set D
v: the total number of discretized attributes.

5. A decision tree generation method for generating a decision tree for determining a type of an internal abnormality of an oil-filled electric apparatus using a computer, the method comprising the steps, by a computer, of:
generating, on the basis of historical abnormality case data of an oil-filled electric apparatus, the historical abnormality case data being stored in performance data storage means, a standardized data group by converting concentrations of a plurality of gas species dissolved in an insulating oil in the oil-filled electric apparatus into ratios for each of abnormality cases, and storing the standardized data group in first standardized data group storage means;

generating, on the basis of the standardized data group of each of the abnormality cases, the standardized data group being stored in the first standardized data group storage means, a discretized data group by converting the ratios of the concentrations of the gas species, the ratios constituting the standardized data group, into a plurality of discretized attributes using predetermined thresholds set for the respective gas species, and storing the discretized data group in first discretized data group storage means; and generating a decision tree for determining a type of an internal abnormality of an oil-filled electric apparatus by analysis using the following formulae (1) to (4) on the basis of the discretized data group of each of the abnormality cases, the discretized data group being stored in the first discretized data group storage means;

[Mathematical 13]

$$G(X) = \frac{M(D) - E(X)}{S(X)} \quad \text{Formula (1)}$$

[Mathematical 14]

$$M(D) = \sum_{i=l}^{n} \left[ -\frac{C_i}{|D|} \log_2 \frac{C_i}{|D|} \right] \quad \text{Formula (2)}$$

[Mathematical 15]

$$E(X) = \sum_{j=l}^{v} \left[ \frac{\alpha_j}{|D|} \sum_{k=l}^{m} \left[ -\frac{\beta_{jk}}{\alpha_j} \log_2 \frac{\beta_{jk}}{\alpha_j} \right] \right] \quad \text{Formula (3)}$$

[Mathematical 16]

$$S(X) = \sum_{j=l}^{v} \left[ -\frac{\alpha_j}{|D|} \log_2 \frac{\alpha_j}{|D|} \right] \quad \text{Formula (4)}$$

X: a gas species dissolved in an insulating oil
D: a set of abnormality case data mapped to a node
|D|: the number of pieces of abnormality case data mapped to a node
$C_i$: the number of the i-th type of internal abnormalities in a set D
$\alpha_j$: the number of pieces of abnormality case data at the j-th branch of a gas species X
$\beta_{jk}$: the number of the k-th type of internal abnormalities at the j-th branch of a gas species X
G (X): a gain ratio
M (D): the amount of expected information with respect to the type of the internal abnormality in a set D
E (X): the amount of expected information after classification by a gas species X
S (X): the amount of expected information with respect to a gas species X in a set D
l: the type or a number of a discretized attribute of the first internal abnormality in the set D
m, n: the total number of types of internal abnormalities in a set D
v: the total number of discretized attributes.

6. A decision tree generation program for generating a decision tree for determining a type of an internal abnormality of an oil-filled electric apparatus using a computer, the program, stored on a non-transitory computer medium, causing the computer to execute the steps of:

generating, on the basis of historical abnormality case data of an oil-filled electric apparatus, the historical abnormality case data being stored in performance data storage means, a standardized data group by converting concentrations of a plurality of gas species dissolved in an insulating oil in the oil-filled electric apparatus into ratios for each of abnormality cases, and storing the standardized data group in first standardized data group storage means;

generating, on the basis of the standardized data group of each of the abnormality cases, the standardized data group being stored in the first standardized data group storage means, a discretized data group by converting the ratios of the concentrations of the gas species, the ratios constituting the standardized data group, into a plurality of discretized attributes using predetermined thresholds set for the respective gas species, and storing the discretized data group in first discretized data group storage means; and generating a decision tree for determining a type of an internal abnormality of an oil-filled electric apparatus by analysis using the following formulae (1) to (4) on the basis of the discretized data group of each of the abnormality cases, the discretized data group being stored in the first discretized data group storage means;

[Mathematical 17]

$$G(X) = \frac{M(D) - E(X)}{S(X)} \quad \text{Formula (1)}$$

[Mathematical 18]

$$M(D) = \sum_{i=l}^{n} \left[ -\frac{C_i}{|D|} \log_2 \frac{C_i}{|D|} \right] \quad \text{Formula (2)}$$

[Mathematical 19]

$$E(X) = \sum_{j=l}^{v} \left[ \frac{\alpha_j}{|D|} \sum_{k=l}^{m} \left[ -\frac{\beta_{jk}}{\alpha_j} \log_2 \frac{\beta_{jk}}{\alpha_j} \right] \right] \quad \text{Formula (3)}$$

[Mathematical 20]

$$S(X) = \sum_{j=l}^{v} \left[ -\frac{\alpha_j}{|D|} \log_2 \frac{\alpha_j}{|D|} \right] \quad \text{Formula (4)}$$

X: a gas species dissolved in an insulating oil
D: a set of abnormality case data mapped to a node
|D|: the number of pieces of abnormality case data mapped to a node
$C_i$: the number of the i-th type of internal abnormalities in a set D
$\alpha_j$: the number of pieces of abnormality case data at the j-th branch of a gas species X
$\beta_{jk}$: the number of the k-th type of internal abnormalities at the j-th branch of a gas species X
G (X): a gain ratio
M (D): the amount of expected information with respect to the type of the internal abnormality in a set D
E (X): the amount of expected information after classification by a gas species X
S (X): the amount of expected information with respect to a gas species X in a set D
l: the type or a number of a discretized attribute of the first internal abnormality in the set D
m, n: the total number of types of internal abnormalities in a set D
v: the total number of discretized attributes.

7. An abnormality diagnosis method of an oil-filled electric apparatus in which an internal abnormality of an oil-filled electric apparatus is diagnosed using a computer, the method comprising the steps, by a computer, of:
generating, on the basis of historical abnormality case data of an oil-filled electric apparatus, the historical abnormality case data being stored in performance data storage means, a standardized data group by converting concentrations of a plurality of gas species dissolved in an insulating oil in the oil-filled electric apparatus into ratios for each of abnormality cases, and storing the standardized data group in first standardized data group storage means;
calculating, on the basis of the standardized data group of each of the abnormality cases, the standardized data group being stored in the first standardized data group storage means, certainty factors corresponding to the respective ratios of the concentrations of the respective gas species, the ratios constituting the standardized data group, using predetermined membership functions set for the respective gas species, generating a discretized data group by converting the ratios of the concentrations of the gas species into a plurality of discretized attributes on the basis of the certainty factors, and storing the discretized data group in first discretized data group storage means;
generating a decision tree for determining a type of an internal abnormality of an oil-filled electric apparatus by analysis using the following formulae (5) to (8) on the basis of the discretized data group of each of the abnormality cases, the discretized data group being stored in the first discretized data group storage means, and storing the decision tree in decision tree storage means;
generating a standardized data group by converting concentrations of a plurality of gas species dissolved in an insulating oil taken from a determination target oil-filled electric apparatus into ratios, and storing the standardized data group in second standardized data group storage means;
generating, on the basis of the standardized data group of the determination target apparatus, the standardized data group being stored in the second standardized data group storage means, a discretized data group by converting the ratios of the concentrations of the gas species, the ratios constituting the standardized data group, into a plurality of discretized attributes on the basis of the same predetermined certainty factors as in the abnormality cases, the predetermined certainty factors being set for the respective gas species, and storing the discretized data group in second discretized data group storage means; and
determining a type of an internal abnormality of the determination target apparatus by using the discretized data group of the determination target apparatus, the discretized data group being stored in the second discretized data group storage means, and the decision tree stored in the decision tree storage means;

[Mathematical 21]

$$G'(X) = \frac{M'(D') - E'(X)}{S'(X)} \quad \text{Formula (5)}$$

[Mathematical 22]

$$M'(D') = \sum_{i=l}^{n} \left[ -\frac{C'_i}{|D'|} \log_2 \frac{C'_i}{|D'|} \right] \quad \text{Formula (6)}$$

[Mathematical 23]

$$E'(X) = \sum_{j=l}^{v} \left[ \frac{\alpha'_j}{|D'|} \sum_{k=l}^{m} \left[ -\frac{\beta'_{jk}}{\alpha'_j} \log_2 \frac{\beta'_{jk}}{\alpha'_j} \right] \right] \quad \text{Formula (7)}$$

[Mathematical 24]

$$S'(X) = \sum_{j=l}^{v} \left[ -\frac{\alpha'_j}{|D'|} \log_2 \frac{\alpha'_j}{|D'|} \right] \quad \text{Formula (8)}$$

X: a gas species dissolved in an insulating oil
D': a set of abnormality case data mapped to a node and based on a certainty factor
|D'|: the sum of certainty factors of abnormality case data mapped to a node
$C_i'$: the sum of certainty factors of the i-th type of internal abnormalities in a set D'
$\alpha_j'$: the sum of certainty factors of abnormality case data at the j-th branch of a gas species X
$\beta_{jk}'$: the sum of certainty factors of the k-th type of internal abnormalities at the j-th branch of a gas species X
G' (X): a gain ratio
M' (D'): the amount of expected information with respect to the type of the internal abnormality in a set D'
E' (X): the amount of expected information after classification by a gas species X
S' (X): the amount of expected information with respect to a gas species X in a set D'
l: the type or a number of a discretized attribute of the first internal abnormality in a set D
m, n: the total number of types of internal abnormalities in a set D
v: the total number of the discretized attributes.

8. An abnormality predictive diagnosis method of an oil-filled electric apparatus in which an internal abnormality of an oil-filled electric apparatus is predictively diagnosed using a computer, the method comprising the steps, by a computer, of:
generating, on the basis of historical abnormality case data of an oil-filled electric apparatus, the historical abnormality case data being stored in performance data storage means, a standardized data group by converting concentrations of a plurality of gas species dissolved in an insulating oil in the oil-filled electric apparatus into ratios for each of abnormality cases, and storing the standardized data group in first standardized data group storage means;
generating, on the basis of the standardized data group of each of the abnormality cases, the standardized data group being stored in the first standardized data group storage means, a discretized data group by converting the ratios of the concentrations of the gas species, the ratios constituting the standardized data group, into a plurality of discretized attributes using predetermined thresholds set for the respective gas species, and storing the discretized data group in first discretized data group storage means;
generating a decision tree for determining a type of an internal abnormality of an oil-filled electric apparatus by analysis using the following formulae (1) to (4) on the basis of the discretized data group of each of the abnormality cases, the discretized data group being stored in the first discretized data group storage means, and storing the decision tree in decision tree storage means;
calculating, with respect to a time series data group of gas concentration, the data group being extracted for each of a plurality of gas species dissolved in an insulation oil in a determination target oil-filled electric apparatus on the basis of three or more pieces of historical performance data of the determination target oil-filled electric apparatus, the performance data being stored in the performance data storage means, a first regression line, dispersion of the time series data group with respect to the first regression line, and uncertainty based on the dispersion, and storing the first regression line, the dispersion and the uncertainty in first regression line data storage means;

calculating, with respect to the latest three or more pieces of the performance data in the time series data group extracted on the basis of the performance data stored in the performance data storage means, a second regression line and a first predicted gas concentration as a gas concentration at a time when a predetermined period of time has passed from the latest measurement time on the second regression line, and storing the second regression line and the first predicted gas concentration in second regression line data storage means;

calculating the sum of the uncertainty stored in the first regression line data storage means and the first predicted gas concentration stored in the second regression line data storage means as a second predicted gas concentration, generating a predicted time series data group composed of the second predicted gas concentration and the latest piece of the performance data in the time series data group extracted on the basis of the performance data stored in the performance data storage means, generating a third regression line with respect to the predicted time series data group, and storing the third regression line in third regression line data storage means;

extracting a third predicted gas concentration at the same time on the third regression line with respect to the third regression line of each of the gas species, the third regression line being stored in the third regression line data storage means, generating a standardized data group by converting third predicted gas concentrations of the gas species into ratios, and storing the standardized data group in second standardized data group storage means;

generating, on the basis of the standardized data group of the determination target apparatus, the standardized data group being stored in the second standardized data group storage means, a discretized data group by converting the ratios of the third predicted gas concentrations of the gas species, the ratios constituting the standardized data group, into a plurality of discretized attributes using the same predetermined thresholds as in the abnormality cases, the predetermined thresholds being set for the respective gas species, and storing the discretized data group in second discretized data group storage means; and determining a type of an internal abnormality of the determination target apparatus by using the discretized data group of the determination target apparatus, the discretized data group being stored in the second discretized data group storage means, and the decision tree stored in the decision tree storage means;

[Mathematical 25]

$$G(X) = \frac{M(D) - E(X)}{S(X)} \quad \text{Formula (1)}$$

[Mathematical 26]

$$M(D) = \sum_{i=l}^{n} \left[ -\frac{C_i}{|D|} \log_2 \frac{C_i}{|D|} \right] \quad \text{Formula (2)}$$

[Mathematical 27]

$$E(X) = \sum_{j=l}^{v} \left[ \frac{\alpha_j}{|D|} \sum_{k=l}^{m} \left[ -\frac{\beta_{jk}}{\alpha_j} \log_2 \frac{\beta_{jk}}{\alpha_j} \right] \right] \quad \text{Formula (3)}$$

[Mathematical 28]

$$S(X) = \sum_{j=l}^{v} \left[ -\frac{\alpha_j}{|D|} \log_2 \frac{\alpha_j}{|D|} \right] \quad \text{Formula (4)}$$

X: a gas species dissolved in an insulating oil

D: a set of abnormality case data mapped to a node

|D|: the number of pieces of abnormality case data mapped to a node $C_i$: the number of the i-th type of internal abnormalities in a set D $\alpha_j$: the number of pieces of abnormality case data at the j-th branch of a gas species X $\beta_{jk}$: the number of the k-th type of internal abnormalities at the j-th branch of a gas species X G (X): a gain ratio M (D): the amount of expected information with respect to the type of the internal abnormality in a set D E (X): the amount of expected information after classification by a gas species X S (X): the amount of expected information with respect to a gas species X in a set D l: the type or a number of a discretized attribute of the first internal abnormality in a set D m, n: the total number of types of internal abnormalities in a set D v: the total number of discretized attributes.

* * * * *